(12) United States Patent
Vecchiotti et al.

(10) Patent No.: US 8,986,188 B2
(45) Date of Patent: Mar. 24, 2015

(54) DYNAMIC AND ADJUSTABLE SUPPORT DEVICES

(75) Inventors: Richard G. Vecchiotti, San Francisco, CA (US); Venita Chandra, Belmont, CA (US); Ross D. Venook, Burlingame, CA (US); Tatum Tarin, Redwood City, CA (US); Joel Goldsmith, Oakland, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1338 days.

(21) Appl. No.: 12/110,911

(22) Filed: Apr. 28, 2008

(65) Prior Publication Data
US 2008/0269548 A1    Oct. 30, 2008

Related U.S. Application Data

(60) Provisional application No. 60/926,561, filed on Apr. 28, 2007.

(51) Int. Cl.
*A61F 2/02*         (2006.01)
*A61F 2/00*         (2006.01)

(52) U.S. Cl.
CPC ....... *A61F 2/0045* (2013.01); *A61F 2250/0001* (2013.01); *A61F 2250/0012* (2013.01); *A61F 2250/0048* (2013.01)
USPC .......................................................... 600/30

(58) Field of Classification Search
CPC ............... A61F 2/0045; A61F 2/0063; A61F 2250/0031; A61F 2250/0051; A61F 2/82; A61F 2002/4495; A61F 2/441; A61F 2250/0012; A61F 2250/0048; A61F 2/02; A61B 2017/00805
USPC ................ 600/29–32, 37; 128/885, 897, 899; 606/151; 623/13.14
See application file for complete search history.

(56) References Cited

U.S. PATENT DOCUMENTS 4,019,499 A    4/1977    Fitzgerald
4,106,511 A    8/1978    Erlandsson
(Continued)

FOREIGN PATENT DOCUMENTS

EP    0 643 945 A2    3/1995
EP    0 643 945 A3    3/1995
(Continued)

OTHER PUBLICATIONS

International Preliminary Report on Patentability mailed on Nov. 12, 2009, for PCT Patent Application No. PCT/US2008/005488, filed on Apr. 28, 2008, 11 pages.
(Continued)

*Primary Examiner* — Christine H Matthews
(74) *Attorney, Agent, or Firm* — Stoel Rives LLP

(57) ABSTRACT

The present invention relates generally to dynamic and/or adjustable support devices, methods of providing dynamic and/or adjustable support to target tissues, and kits comprising these devices. These devices may have particular utility in providing support to the urethra. The dynamic support devices generally comprise at least one attachment member for attachment to bodily tissue, and at least one expandable member capable of assuming an unexpanded configuration and an expanded configuration. The adjustable support devices generally comprise at least one attachment member for attachment to bodily tissue, and at least one shape-changing portion that is capable of assuming first and second configurations, each with different shapes. Additionally, the dynamic support devices may comprise features of the adjustable support devices, and vice versa.

24 Claims, 15 Drawing Sheets

(56) References Cited

U.S. PATENT DOCUMENTS

| | | |
|---|---|---|
| 4,194,508 A | 3/1980 | Anderson |
| 4,248,214 A | 2/1981 | Hannah et al. |
| 4,248,229 A | 2/1981 | Miller |
| 4,428,365 A | 1/1984 | Hakky |
| 4,705,029 A | 11/1987 | Borodulin et al. |
| 4,739,759 A | 4/1988 | Rexroth et al. |
| 4,760,840 A | 8/1988 | Fournier, Jr. et al. |
| 4,846,817 A | 7/1989 | Mohr et al. |
| 4,911,149 A | 3/1990 | Borodulin et al. |
| 5,030,199 A | 7/1991 | Barwick et al. |
| 5,149,326 A | 9/1992 | Woodgrift et al. |
| 5,193,553 A | 3/1993 | Kalinoski |
| 5,342,374 A | 8/1994 | Wan et al. |
| 5,366,490 A | 11/1994 | Edwards et al. |
| 5,370,675 A | 12/1994 | Edwards et al. |
| 5,507,754 A | 4/1996 | Green et al. |
| 5,514,176 A | 5/1996 | Bosley, Jr. |
| 5,518,504 A | 5/1996 | Polyak |
| 5,542,915 A | 8/1996 | Edwards et al. |
| 5,549,617 A | 8/1996 | Green et al. |
| 5,554,110 A | 9/1996 | Edwards et al. |
| 5,562,598 A | 10/1996 | Whalen et al. |
| 5,562,689 A | 10/1996 | Green et al. |
| 5,593,389 A | 1/1997 | Chang |
| 5,599,294 A | 2/1997 | Edwards et al. |
| 5,652,842 A | 7/1997 | Siegrist, Jr. et al. |
| 5,685,839 A | 11/1997 | Edwards et al. |
| 5,704,893 A | 1/1998 | Timm |
| 5,800,378 A | 9/1998 | Edwards et al. |
| 5,899,909 A | 5/1999 | Claren et al. |
| 5,934,283 A | 8/1999 | Willem et al. |
| 5,934,286 A | 8/1999 | Maginot |
| 5,964,727 A | 10/1999 | Edwards et al. |
| 5,964,806 A | 10/1999 | Cook et al. |
| 5,984,910 A | 11/1999 | Berke |
| 5,993,472 A | 11/1999 | Hermann et al. |
| 6,036,635 A | 3/2000 | Altshuler |
| 6,042,534 A | 3/2000 | Gellman et al. |
| 6,045,498 A | 4/2000 | Burton et al. |
| 6,074,341 A | 6/2000 | Anderson et al. |
| 6,095,969 A | 8/2000 | Karram et al. |
| 6,104,959 A | 8/2000 | Spertell |
| 6,117,067 A | 9/2000 | Gil-Vernet |
| 6,124,461 A | 9/2000 | Shoemaker |
| 6,129,726 A | 10/2000 | Edwards et al. |
| 6,139,544 A | 10/2000 | Mikus et al. |
| 6,159,170 A | 12/2000 | Borodulin et al. |
| 6,190,407 B1 | 2/2001 | Ogle et al. |
| 6,210,419 B1 * | 4/2001 | Mayenberger et al. ....... 606/158 |
| 6,248,101 B1 | 6/2001 | Whitmore, III et al. |
| 6,267,782 B1 | 7/2001 | Ogle et al. |
| 6,273,852 B1 | 8/2001 | Lehe et al. |
| 6,328,687 B1 | 12/2001 | Karram et al. |
| 6,342,049 B1 | 1/2002 | Nichols |
| 6,365,590 B1 | 4/2002 | Shoemaker |
| 6,366,814 B1 | 4/2002 | Boveja et al. |
| 6,382,214 B1 | 5/2002 | Raz et al. |
| 6,406,423 B1 | 6/2002 | Scetbon |
| 6,419,624 B1 | 7/2002 | Burton et al. |
| 6,419,653 B2 | 7/2002 | Edwards et al. |
| 6,419,701 B1 | 7/2002 | Cook et al. |
| 6,478,727 B2 | 11/2002 | Scetbon |
| 6,485,422 B1 | 11/2002 | Mikus et al. |
| 6,491,703 B1 | 12/2002 | Ulmsten |
| 6,500,194 B2 | 12/2002 | Benderev et al. |
| 6,506,190 B1 | 1/2003 | Walshe |
| 6,530,879 B1 | 3/2003 | Adamkiewicz |
| 6,575,897 B1 | 6/2003 | Ory et al. |
| 6,579,224 B1 | 6/2003 | Burton et al. |
| 6,582,451 B1 * | 6/2003 | Marucci et al. ............... 606/207 |
| 6,596,010 B1 | 7/2003 | Hermann et al. |
| 6,610,054 B1 | 8/2003 | Edwards et al. |
| 6,612,977 B2 | 9/2003 | Staskin et al. |
| 6,638,211 B2 | 10/2003 | Suslian et al. |
| 6,645,138 B2 | 11/2003 | Cook et al. |
| 6,648,921 B2 | 11/2003 | Anderson et al. |
| 6,684,108 B2 | 1/2004 | Surbeck et al. |
| 6,702,827 B1 | 3/2004 | Lund et al. |
| 6,709,385 B2 | 3/2004 | Forsell |
| 6,786,542 B1 | 9/2004 | Nuzzarello |
| 6,814,712 B1 | 11/2004 | Edwards et al. |
| 6,830,052 B2 | 12/2004 | Carter et al. |
| 6,830,588 B2 * | 12/2004 | Furukawa et al. ......... 623/14.13 |
| 6,852,091 B2 | 2/2005 | Edwards et al. |
| 6,879,859 B1 | 4/2005 | Boveja |
| 6,911,002 B2 | 6/2005 | Fierro |
| 6,911,003 B2 | 6/2005 | Anderson et al. |
| 6,953,428 B2 | 10/2005 | Gellman et al. |
| 6,969,380 B1 | 11/2005 | Zunker |
| 6,971,986 B2 | 12/2005 | Staskin et al. |
| 7,014,606 B2 | 3/2006 | Burton et al. |
| 7,037,317 B2 | 5/2006 | Hermann et al. |
| 7,056,288 B2 | 6/2006 | Tracey et al. |
| 7,056,333 B2 | 6/2006 | Walshe |
| 7,083,637 B1 | 8/2006 | Tannhauser |
| 7,087,055 B2 | 8/2006 | Lim et al. |
| 7,128,707 B2 | 10/2006 | Banik |
| 7,163,506 B2 | 1/2007 | Grise |
| 7,204,801 B2 | 4/2007 | Grocela |
| 7,223,228 B2 | 5/2007 | Timm et al. |
| 7,776,061 B2 * | 8/2010 | Garner et al. ................. 606/151 |
| 7,815,562 B2 * | 10/2010 | Chu ............................... 600/30 |
| 7,871,416 B2 * | 1/2011 | Phillips ........................ 606/151 |
| 7,981,023 B2 | 7/2011 | Nowlin et al. |
| 2001/0018549 A1 | 8/2001 | Scetbon |
| 2001/0031941 A1 | 10/2001 | Edwards et al. |
| 2002/0028181 A1 | 3/2002 | Miller et al. |
| 2002/0050769 A1 | 5/2002 | Pelrine et al. |
| 2002/0099258 A1 | 7/2002 | Staskin et al. |
| 2002/0099259 A1 | 7/2002 | Anderson et al. |
| 2002/0103518 A1 | 8/2002 | Surbeck et al. |
| 2002/0129822 A1 | 9/2002 | Furukawa et al. |
| 2002/0147382 A1 | 10/2002 | Neisz et al. |
| 2002/0151763 A1 | 10/2002 | Cook et al. |
| 2002/0156342 A1 | 10/2002 | Burton et al. |
| 2002/0165566 A1 | 11/2002 | Ulmsten |
| 2002/0183740 A1 | 12/2002 | Edwards et al. |
| 2002/0188170 A1 * | 12/2002 | Santamore et al. ............. 600/37 |
| 2003/0023144 A1 | 1/2003 | Tracey et al. |
| 2003/0036676 A1 | 2/2003 | Scetbon |
| 2003/0045774 A1 | 3/2003 | Staskin et al. |
| 2003/0062052 A1 | 4/2003 | Carter et al. |
| 2003/0078604 A1 | 4/2003 | Walshe |
| 2003/0152522 A1 | 8/2003 | Miller et al. |
| 2003/0195545 A1 | 10/2003 | Hermann et al. |
| 2003/0199732 A1 | 10/2003 | Suslian et al. |
| 2004/0006353 A1 | 1/2004 | Bosley, Jr. et al. |
| 2004/0015045 A1 | 1/2004 | Burton et al. |
| 2004/0049408 A1 | 3/2004 | Voss et al. |
| 2004/0068203 A1 | 4/2004 | Gellman et al. |
| 2004/0096422 A1 | 5/2004 | Schwartz et al. |
| 2004/0102770 A1 | 5/2004 | Goble |
| 2004/0143152 A1 | 7/2004 | Grocela |
| 2004/0144394 A1 | 7/2004 | Dauner et al. |
| 2004/0144395 A1 | 7/2004 | Evans et al. |
| 2004/0147886 A1 | 7/2004 | Bonni |
| 2004/0249396 A1 | 12/2004 | Lund et al. |
| 2004/0254625 A1 | 12/2004 | Stephens et al. |
| 2004/0267088 A1 * | 12/2004 | Kammerer ..................... 600/37 |
| 2005/0010203 A1 | 1/2005 | Edwards et al. |
| 2005/0027160 A1 | 2/2005 | Siegel et al. |
| 2005/0027161 A1 | 2/2005 | Cook et al. |
| 2005/0038452 A1 | 2/2005 | Chu |
| 2005/0070816 A1 | 3/2005 | Coats |
| 2005/0101834 A1 | 5/2005 | Merade |
| 2005/0131274 A1 | 6/2005 | Suslian et al. |
| 2005/0171583 A1 | 8/2005 | Mosher et al. |
| 2005/0222559 A1 | 10/2005 | Shiono et al. |
| 2005/0245787 A1 | 11/2005 | Cox et al. |
| 2005/0250978 A1 | 11/2005 | Kammerer |
| 2005/0256364 A1 | 11/2005 | Burton et al. |
| 2005/0261547 A1 | 11/2005 | Bouffier |
| 2005/0277806 A1 | 12/2005 | Cristalli |
| 2006/0004246 A1 | 1/2006 | Selikowitz |

(56) References Cited

U.S. PATENT DOCUMENTS

| | | |
|---|---|---|
| 2006/0015001 A1 | 1/2006 | Staskin et al. |
| 2006/0041185 A1 | 2/2006 | Browning |
| 2006/0058574 A1 | 3/2006 | Priewe et al. |
| 2006/0058830 A1 | 3/2006 | Hermann et al. |
| 2006/0069301 A1 | 3/2006 | Neisz et al. |
| 2006/0089525 A1 | 4/2006 | Mamo et al. |
| 2006/0112536 A1 | 6/2006 | Herweck et al. |
| 2006/0134168 A1 | 6/2006 | Chappa et al. |
| 2006/0195006 A1 | 8/2006 | Daurelle et al. |
| 2006/0195007 A1 | 8/2006 | Anderson et al. |
| 2006/0199996 A1 | 9/2006 | Caraballo et al. |
| 2006/0235447 A1 | 10/2006 | Walshe |
| 2006/0252980 A1 | 11/2006 | Arnal et al. |
| 2006/0264698 A1 | 11/2006 | Kondonis et al. |
| 2006/0281964 A1 | 12/2006 | Burton et al. |
| 2006/0281966 A1 | 12/2006 | Peacock, III |
| 2006/0287570 A1 | 12/2006 | Whalen et al. |
| 2007/0015957 A1 | 1/2007 | Li |
| 2007/0021649 A1 | 1/2007 | Nowlin et al. |
| 2007/0032695 A1 | 2/2007 | Weiser |
| 2007/0038017 A1 | 2/2007 | Chu |
| 2007/0049790 A1 | 3/2007 | Wagner et al. |
| 2007/0049791 A1 | 3/2007 | Merade et al. |
| 2007/0156012 A1 | 7/2007 | Tracey et al. |
| 2007/0162120 A1 | 7/2007 | Bouffier |
| 2007/0270827 A1* | 11/2007 | Lim et al. ............... 606/61 |
| 2008/0004487 A1 | 1/2008 | Haverfield |
| 2008/0009665 A1* | 1/2008 | Merade et al. ........... 600/30 |
| 2008/0045782 A1 | 2/2008 | Jimenez |
| 2010/0198000 A1 | 8/2010 | Wagner et al. |
| 2010/0261950 A1 | 10/2010 | Lund et al. |

FOREIGN PATENT DOCUMENTS

| | | |
|---|---|---|
| EP | 1 238 638 A1 | 9/2002 |
| EP | 1 238 638 B1 | 9/2002 |
| JP | 2002-263125 A | 9/2002 |
| WO | WO-01/145589 A1 | 6/2001 |
| WO | WO-02/078552 A1 | 10/2002 |
| WO | WO-2005/122954 A1 | 12/2005 |
| WO | WO-2007/018532 A1 | 2/2007 |
| WO | WO-2007/022065 A2 | 2/2007 |
| WO | WO-2007/022065 A3 | 2/2007 |
| WO | WO-2008/134064 A1 | 11/2008 |
| WO | WO-2009/023256 A2 | 2/2009 |
| WO | WO-2009/023256 A3 | 2/2009 |

OTHER PUBLICATIONS

International Search Report mailed on Aug. 13, 2008, for PCT Application No. PCT/US2008/005488, filed on Apr. 28, 2008, six pages.
Written Opinion mailed on Aug. 13, 2008, for PCT Application No. PCT/US2008/005488, filed on Apr. 28, 2008, nine pages.
International Search Report mailed on Feb. 23, 2009, for PCT Patent Application No. PCT/US2008/009748, filed on Aug. 14, 2008, 7 pages.
Non-Final Office Action mailed on Sep. 6, 2011, for U.S. Appl. No. 12/191,980, filed on Aug. 14, 2008, 11 pages.
Written Opinion of the International Searching Authority, mailed on Feb. 23, 2009, for PCT Patent Application No. PCT/US2008/009748, filed on Aug. 14, 2008, 9 pages.
Yamana, T. et al. (Nov. 2004, e-pub. Oct. 11, 2004). "Perineal Puborectalis Sling Operation for Fecal Incontinence: Preliminary Report," *Dis Colon Rectum* 47(11):1983-1989.
Final Office Action mailed on Mar. 21, 2013, for U.S. Appl. No. 12/191,980, filed Aug. 14, 2008, 12 pages.
Non-Final Office Action mailed on Jun. 12, 2012, for U.S. Appl. No. 12/191,980, filed Aug. 14, 2008, 11 pages.

* cited by examiner

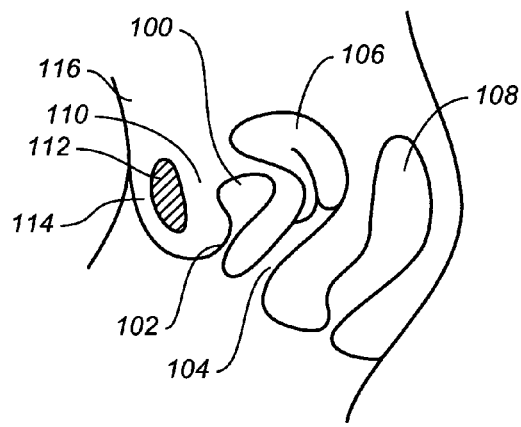
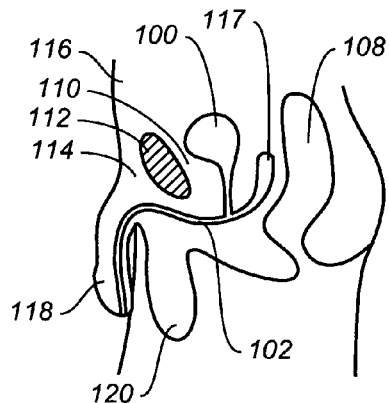
FIG. 1A  FIG. 1B
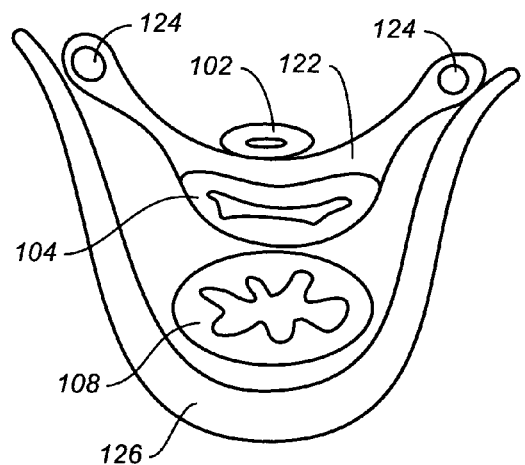
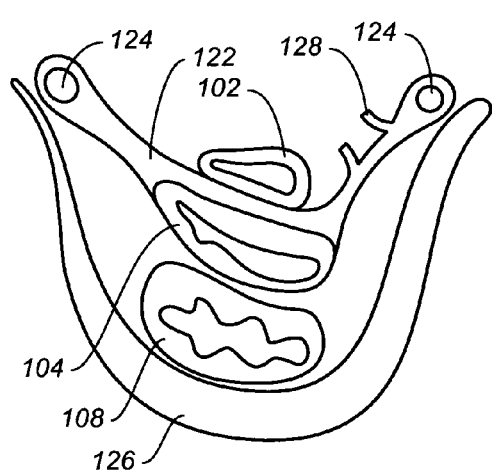
FIG. 1C  FIG. 1D

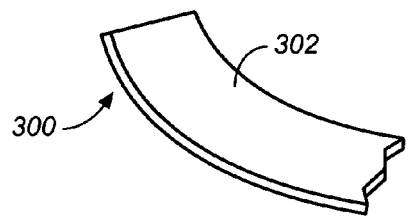 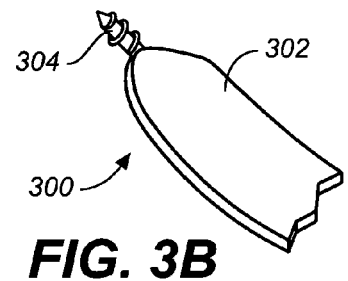
FIG. 3A   FIG. 3B
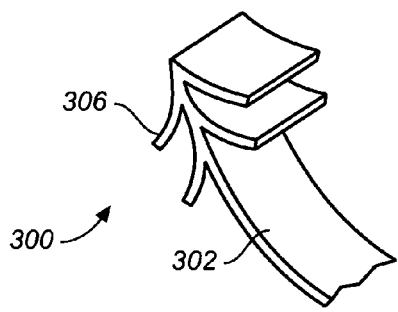 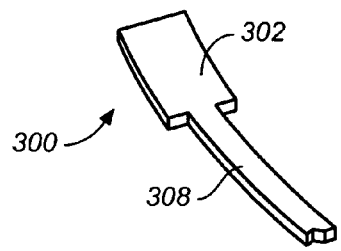
FIG. 3C   FIG. 3D
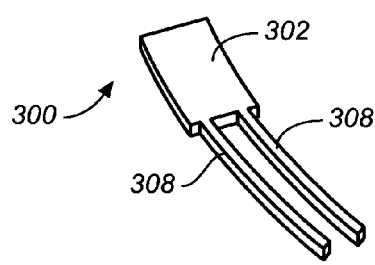 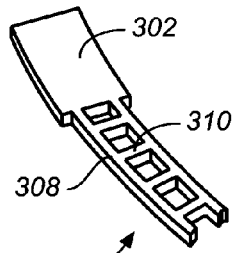
FIG. 3E   FIG. 3F
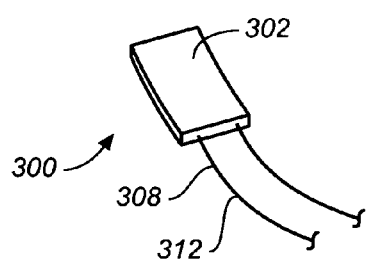
FIG. 3G

DYNAMIC AND ADJUSTABLE SUPPORT DEVICES

CROSS-REFERENCE TO RELATED APPLICATIONS

This application claims priority to U.S. Provisional Pat. App. No. 60/926,561 filed Apr. 28, 2007, the entirety of which is hereby incorporated by reference herein.

FIELD

The present invention relates generally to devices that provide dynamic and/or adjustable support to an anatomic location, methods of using the devices, and kits including them. The methods, devices, and kits described here may find particular utility in the area of incontinence.

BACKGROUND OF THE INVENTION

Loss of bladder control, also known as urinary incontinence, is a widespread, debilitating condition, affecting millions. Associated with symptoms such as sleep deprivation, urosepsis, and skin irritation, urinary incontinence can have significant physiological, psychological, and social impacts on quality of life. The most common form of urinary incontinence, stress urinary incontinence, involves the involuntary leakage of urine upon sneezing, coughing, or other exertion. This leakage generally occurs when an increase in abdominal pressure during a stress event overcomes the body's urinary continence mechanisms.

During urination, muscles in the bladder contract and force urine from the bladder into the urethra. At the same time, the musculature of the urethral wall and the urinary sphincter relax, allowing urine to pass through the urethra and out of the body. During other activity, the urinary sphincter and the musculature of the urethral wall remain contracted, coapting the urethra. The urethra is further supported by a hammock-like pelvic floor which includes endopelvic fascia and, in women, the anterior vaginal wall. Generally, increases in abdominal pressure (generated, for example, by stress events such as coughing or exertion) push the urethra against the pelvic floor, further coapting the urethra.

Stress urinary incontinence is thought to occur by one, or both, of two mechanisms. The first mechanism results from failure of the urinary sphincter and musculature of the urethral wall. In this mechanism, called intrinsic sphincter deficiency, the urethral sphincter muscles are unable to adequately constrict the urethra, which results in urine loss during stress events. Intrinsic sphincter deficiency may result from operative trauma, scarring, denervation or atrophy. The second mechanism, urethral hypermobility, occurs when support structures within the pelvic floor become weakened or damaged. In these cases, the pelvic floor no longer properly functions to compress the urethra upon increases in abdominal pressure.

Fecal incontinence results from a loss of bowel control and an inability to hold stool within the body. During defecation, muscles in the rectum contract and force stool through the anus. Simultaneously, sphincters of the anus relax, thereby allowing stool to pass out of the body. During other activity, the anal sphincters remain contracted, preventing passage of stool therethrough.

Fecal incontinence is thought to be caused by one, or more, of a number of mechanisms. Constipation can result in the stretching and eventual weakening of the rectal muscles, which makes the rectum unable to adequately contain stool. Similarly, physical damage to the internal or external anal sphincters may result in a similar effect. In some situations, nerve damage resulting from childbirth, a stroke or physical injury may prevent the anal sphincters from functioning properly.

Given the widespread and debilitating nature of urinary and fecal incontinence, additional devices for treating urinary and fecal incontinence would be desirable. In particular, adjustable devices, which may allow physicians to change, following or during implantation, the amount of support a device provides would be desirable. Devices that dynamically provide different levels of support during times of stress would also be desirable.

BRIEF SUMMARY OF THE INVENTION

Described here are dynamic and/or adjustable support devices, methods of using them, and kits that may incorporate them. The devices may be useful in a variety of locations within the body, for a number of different functions. In some of the devices described here, the devices have first and second attachment members and at least one expandable member positioned therebetween, where the expandable member has an unexpanded configuration and an expanded configuration. In these variations, the devices are configured to apply a supporting force to the tissue when the expandable member is in its expanded configuration. In some variations, the expandable member changes from its unexpanded configuration to its expanded configuration by application of a first force to one or more of the attachment members. In some variations, the first force applied to the attachment members may be a displacement force. In some variations, the attachment members are configured to translate the first force into a second force. This second force may be, for example, a tensile force. In some variations, the supporting force applied by the expandable member is a compressive force. This supporting force may be applied to a number of tissues, for example, urethral tissue, rectal tissue, etc.

Generally, the expandable members described here may be made of any suitable or useful material. In some variations, for example, the expandable member comprises a shape memory material. In other variations, the expandable member comprises a stimulus responsive material. In still other variations, the expandable member comprises a shape-resilient material. In some variations, the expandable member comprises a mesh. Of course, the expandable member may comprise some combination of these, or other, materials.

Furthermore, the expandable member may be any suitable structure that is capable of assuming expanded and unexpanded configurations. In some variations, the expandable member comprises a first hinged portion attached to a second hinged portion. In other variations, the expandable member comprises first and second hinged portions attached to a base portion. In some of these variations, the expandable member further comprises a third hinged portion attached to the first hinged portion and a fourth hinged portion attached to the second hinged portion. In other variations, the expandable member comprises one or more flexible flaps.

In some of the variations described here, the expandable member comprises an expandable membrane. For example, in variations where the device comprises first and second hinged portions attached to a base portion, the expandable member may further comprise an expandable membrane attached to the first and second hinged portions. The expandable member may also comprise a cover. The cover may be made of any suitable material. For example, the cover may comprise silicone.

In general, the expandable members of these variations may take on any suitable shape when in their expanded configurations and their unexpanded configurations. In some variations, for example, the expandable member may be substantially flat when in its unexpanded configuration. In other variations, the expandable member may be approximately trapezoidal in shape when in its expanded configuration.

The attachment members described here may be made of any suitable or useful materials. In some variations, for example, one or more of the attachment members may comprise one or more tissues or synthetic materials. In other variations, one or more of the attachment members may comprise polypropylene. In some variations, one or more of the attachment members may comprise a mesh. Of course, the attachment members may comprise some combination of these or other materials.

Similarly, the attachment members described here may take on any suitable structure. For example, the first and second attachment members may be approximately rectangular. These members may be of any suitable size, for example, between about 1 and about 4 cm in width and between about 5 and about 20 cm in length. Furthermore, one or more of the attachment members may promote tissue ingrowth. In some variations, one or more of the attachment members may comprise an anchoring component. In some of these variations, one or more of the attachment members may comprise at least one connection member for connecting the anchoring component to the expandable member.

In other devices described here, the devices comprise at least one attachment member for attachment to bodily tissue and at least one non-inflatable expandable member connected to the at least one attachment member. In these variations, the expandable member has an unexpanded configuration and an expanded configuration, and the expandable member in its expanded configuration is configured to provide support to a target tissue. In some variations, this tissue is urethral tissue. In other variations, the tissue is rectal tissue. The at least one attachment member and at least one expandable member may take on any suitable geometry and may be made from any suitable material, as described above. In some of these devices, the expandable member is configured to change from its unexpanded configuration to its expanded configuration upon the application of at least one stimulus to the expandable member. The at least one stimulus may be any suitable stimulus. For example, in some of the devices described here, the at least one stimulus is selected from the group consisting of a temperature change, a pH change, an optical stimulus (including light), and combinations thereof. In other variations, the at least one stimulus is selected from the group consisting of RF energy, microwave energy, electrical energy, magnetic energy, mechanical energy, and combinations thereof.

In other variations, the devices described here comprise at least one attachment member for attachment to bodily tissue and at least one non-inflatable expandable member, where the at least one attachment member is configured to translate an initial force into a tensile force to expand the expandable member. In some of these variations, the tensile force is substantially normal to the initial force. The at least one attachment member and at least one expandable member may have any suitable geometry, and may be made from any suitable material as described above.

In some variations, the devices described here comprise one or more attachment members and a non-inflatable, shape-changing portion therebetween, where the shape-changing portion has a first configuration and a second configuration, and where the shape-changing portion changes from the first configuration to the second configuration upon an application of at least one stimulus to the shape-changing portion. In these variations, the at least one stimulus is not provided by the one or more attachment members. In some variations of these devices, the shape-changing portion comprises a member that increases in length upon the application of the at least one stimulus. In other variations, the shape-changing portion comprises a member that decreases in length upon the application of the at least one stimulus. Generally, the at least one stimulus may be any suitable stimulus. For example, in some of the devices described here, one or more of the at least one stimulus may be selected from the group consisting of a temperature change, a pH change, an optical stimulus, and combinations thereof. In other devices, one or more of the at least one stimulus is selected from the group consisting of RF energy, microwave energy, electrical energy, magnetic energy, mechanical energy, and combinations thereof. In still other devices, one or more of the at least one stimulus is a physical force.

In some of the devices, the shape-changing portion comprises a leaf spring. In some variations, the shape-changing portion comprises a first and a second shape memory material. In some of these variations, the at least one stimulus comprises a first stimulus and a second stimulus, where the shape-changing portion changes from the first configuration to the second configuration upon application of the first stimulus to the first shape memory material, and the shape-changing portion changes from the second configuration to the first configuration upon application of the second stimulus to the second shape memory material. In some variations, the shape-changing portion comprises a shape memory alloy, for example, a nickel-titanium alloy.

Methods of supporting tissues are also described here. In general, the methods comprise implanting a device into a patient to support a target tissue. In some methods, the device comprises first and second attachment members and at least one expandable member positioned therebetween, where the expandable member has an unexpanded configuration and an expanded configuration, and where the expandable member changes from its unexpanded configuration to its expanded configuration by application of a force to one or more of the attachment members. In some of these methods, the expandable member is placed underneath the target tissue.

In some methods, implanting the device comprises attaching one or more of the attachment members to soft tissues. In other methods, implanting the device comprises attaching one or more of the attachment members to bony structures (e.g., pelvic bony structures). The device may be implanted by any number of approaches. The device may be implanted, for example, using a transvaginal approach, using a transperineal approach, and the like.

In some variations, implanting the device comprises passing the first attachment member through a first obturator foramen and passing the second attachment member through a second obturator foramen. In other variations, implanting the device comprises securing an end of the first attachment member in tissue within or external to a first obturator foramen and securing an end of the second attachment member in tissue within or external to a second obturator foramen.

In some variations, implanting the device comprises positioning the device such that at least a portion of each of the first and second attachment members are located in the retropubic space. In other variations, implanting the device comprises positioning the device such that at least a portion of each of the first and second attachment members are located in the prepubic space.

In some of the methods described here, the devices utilized comprise at least one attachment member for attachment to bodily tissue and at least one non-inflatable expandable member connected to the at least one attachment member. The expandable member has an unexpanded configuration and an expanded configuration, and the expandable member is configured to provide support to tissue in its expanded configuration. In some of these methods, the tissue is urethral tissue. In other methods, the tissue is rectal tissue. The device may be implanted in any fashion as described above.

In still other methods, the devices utilized comprise at least one attachment member for attachment to bodily tissue, and at least one non-inflatable expandable member, where the at least one attachment member is configured to translate an initial force into a tensile force to expand the expandable member. In some of these methods, implanting the device comprises placing the expandable member underneath, adjacent to, or around urethral or rectal tissue. The device may be implanted in any fashion as described above.

In other methods, the devices utilized comprise one or more attachment members and a non-inflatable, shape-changing portion therebetween, where the shape-changing portion has a first configuration and a second configuration, where the shape-changing portion changes from the first configuration to the second configuration upon application of a stimulus to the shape-changing portion. In these variations, the stimulus is not provided by the one or more attachment members. The device may be implanted in any fashion as described above.

BRIEF DESCRIPTION OF THE DRAWINGS

FIGS. 1A-1D are simplified depictions of the pelvic anatomy. FIG. 1A is a side view of the female pelvic anatomy. FIG. 1B is a side view of the male pelvic anatomy. FIGS. 1C and 1D are transverse cross-sections of the female pelvic anatomy.

FIGS. 3A-3G are depictions of variations of attachment members.

DETAILED DESCRIPTION OF THE INVENTION

Figure 2A:
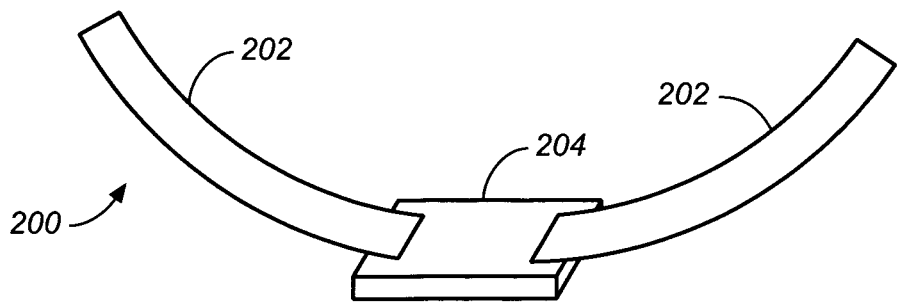
FIGS. 2A and 2B are perspective views of one variation of a dynamic support device including attachment members and an expandable member.

Described here are devices and methods for providing dynamic or adjustable support to a target tissue, as well as kits including that may comprise such devices. In some variations, the support devices provide dynamic support to an anatomical location. When reference is made to the term "support" herein, it should be understood that such support can include, without limitation, actions such as holding, compressing, coapting, moving, relocating, and any combinations of the foregoing, and the like. In other variations, the support devices provide static support to an anatomical location that can be adjusted during or after implantation. In still other variations, the support devices provide dynamic support to an anatomical location that can be adjusted during or after implantation. These devices may be useful in providing support to any number of tissues, but may have particular utility in providing support to the urethra. Thus it may be helpful to briefly describe the anatomy of the pelvic region.

FIGS. 1A-1D provide simplified depictions of the anatomy of the pelvic region. FIG. 1A shows a side view of the female pelvic anatomy. Shown there is bladder (100), urethra (102), vagina (104), uterus (106), rectum (108), retropubic space (110), pubic symphysis (112), prepubic space (114), and rectus fascia (116). FIG. 1B shows a side view of the male pelvic anatomy. Shown there is bladder (100), urethra (102), seminal vesicle (117), rectum (108), retropubic space (110), pubic symphysis (112), prepubic space (114), rectus fascia (116), penis (118) and testes (120). FIG. 1C shows a transverse cross section of the female pelvic anatomy, including urethra (102), vagina (104) and rectum (108). Additionally shown there is endopelvic fascia (122) connecting the vagina (104) to arcus tendineus fasciae pelvis (124), and pubococcygeus muscle (126). FIG. 1D shows a transverse cross section of the female pelvic anatomy of a patient suffering from urethral hypermobility caused by torn ligament (128) in the endopelvic fascia (122).

Some variations of the devices described here are devices that provide dynamic support to a target tissue. Generally, these devices comprise at least one attachment member for attachment to bodily tissues. These devices also comprise an expandable member that has an unexpanded configuration and an expanded configuration. These expandable members generally apply a force to a target bodily tissue when the expandable member is in its expanded configuration.

Figure 2B:
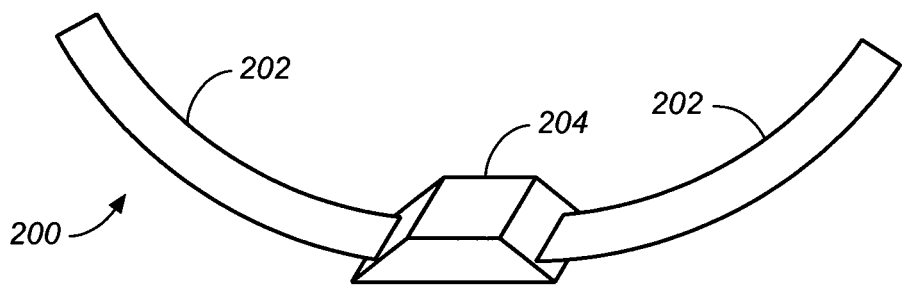
Figure 2C:
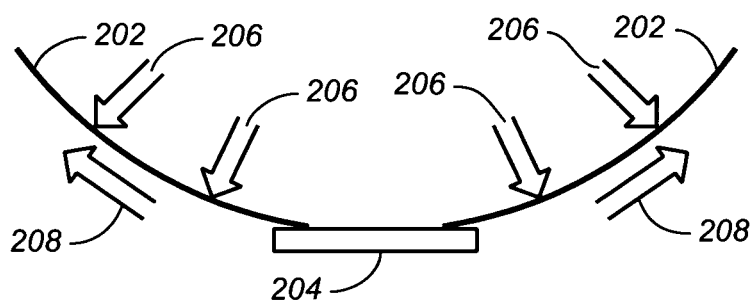
FIG. 2C is a side view of the same dynamic support device.

FIGS. 2A-2C illustrate one variation of a dynamic support device (200), including attachment members (202) and expandable member (204). Generally, the expandable member (204) expands from its unexpanded configuration, as shown in FIG. 2A, to its expanded configuration, as shown in FIG. 2B, upon the application of a force to one or more of the attachment members (202). In other variations, the expandable member (204) may change between its unexpanded and expanded configurations upon application of a stimulus to the expandable member (204).

Generally, the support device (200) has at least one attachment member (202) and at least one expandable member (204). In some variations, the support device (200) may have two or more attachment members (202), or may have two or more expandable members (204). The attachment members (202) may be integrally formed with the expandable members (204), or may be separate components attached to the expandable members (204). In some variations, additional components, such as a force sensor (not shown), may be positioned between the attachment members (202) and the expandable members (204), or between the expandable members (204).

In some variations, the attachment members (202) are attached to bodily tissues during or after implantation of the device (200). After implantation, bodily tissues may apply forces to the attachment members (202). For example, when the device (200) is implanted within the pelvic anatomy, downward movement of the pelvic tissues due to increases in abdominal pressure during a stress event may place an initial force (206) on the attachment members (202). This initial force (206) may then cause a tensile force (208) in the attachment members (202), as illustrated in FIG. 2C. This tensile force (208) may, for example, be substantially normal to the initial force (206). Additionally, this tensile force (208) may be applied to the expandable member (204), which may cause the expandable member (204) to expand from its unexpanded configuration to its expanded configuration.

Attachment members may take on any suitable configuration. In some variations, the attachment members are able to translate a first force applied thereto into a second force. In other variations, the attachment members are able to translate a force applied thereto into a stimulus. For example, the attachment member may comprise a piezoelectric material that creates a voltage when a force places the attachment member under stress. In some variations, the attachment members are flexible, or contain flexible components.

Any of the attachment members described here may have one or more additional components or members, e.g., anchoring components, connecting members, etc. Illustrative examples of suitable attachment members are shown in FIGS. 3A-3G. In some variations, as shown in FIG. 3A, an attachment member (300) comprises a strip of material (302) without a separate or distinct anchoring component. Material (302) may be made of any suitable biocompatible material. Examples of suitable materials include, but are not limited to, polypropylene, polyethylene, polyester, polycarbonate, polyetheretherketone, polyurethane, polyvinyl chloride, polyethylene terephthalate and silicone. In some variations, material (302) comprises a mesh. In other variations, material (302) includes autologous tissue, homologous tissue, cadaveric tissue, xenograft tissue, collagen matrix materials, synthetic materials, or a combination thereof. In still other variations, material (302) is a bioabsorbable material. While shown in FIG. 3A as generally rectangular, attachment member (300) may have any suitable shape or geometry (e.g., generally circular, generally square, generally elliptical, etc.). In some variations, attachment member (300) may be between about 1 cm and about 4 cm in width, and between about 5 cm and about 20 cm in length.

The attachment member (300) may be configured to promote tissue ingrowth. For example, attachment member (300) may contain ridges, rough edges or other protrusions attached thereto, formed therefrom or formed thereupon for promoting tissue ingrowth. In some variations, attachment member (300) may comprise scar-promoting materials, adhesion promoting materials, or a combination thereof. Attachment member (300) may also be coated or impregnated with a chemical or material that promotes tissue ingrowth. In variations in which the attachment member (300) comprises or includes a mesh, the mesh may have frayed edges or may have protruding edge threads incorporated into the mesh itself. In other variations where the attachment member comprises or includes a mesh, abrasive materials may be woven into the mesh to encourage scarring. In still other variations, the mesh may have pores of a size large enough to allow for tissue ingrowth through the pores.

The attachment member (300) may also have one or more integral or separate structures or anchoring components to help anchor or secure it to either soft or bony tissues. In some variations, as shown in FIG. 3B, attachment member (300) comprises a bone screw (304), which may be attached to material (302) as shown there. In other variations, an anchoring component may comprise a hook, clip, staple, or barb, or other anchoring feature. In still other variations, as shown in FIG. 3C, for example, anchoring component (306) may include flaring flaps or a barbed like protrusion. While shown in FIG. 3C as being integral with material (302), flaring flaps (306) may be made distinct from material (302), and may be made from distinct material. The flaring flaps (306) may allow the attachment member (300) to move freely in one direction while resisting movement in the opposite direction, and may allow for the implantation of a support device without making skin incisions, as described below. In other variations, prongs or hooks may be attached to or formed upon an anchoring component. These structures may also allow the attachment member (300) to move freely in one direction while resisting movement in the opposite direction.

The attachment member (300) may also include one or more connection members (308) for attaching various features or components of the attachment member (300) to the expandable member, as shown for example, in FIG. 3D. While shown in FIG. 3D as having one connection member (308), attachment member (300) may contain any number of connection members (308). Also it should be understood that the connection member (308) may be made from the same or different material (302) as the rest of the attachment member (300). For example, as illustrated in FIG. 3E, attachment member (300) may comprise two connection members (308). In variations with two or more connection members (308), the attachment member (300) may additionally include links (310) spanning the connection members (308), as shown in FIG. 3F. Connection members (308) and links (310) may be made of any suitable biocompatible material or combination of materials as described above. It should also be understood that while shown in FIG. 3D as being substantially flat and rectangular, connection member (308) need not be. Indeed, connection members (308) may take on any shape or geometry, including, but not limited to, cylindrical, circular, elliptical, cubical, etc. In some variations, as shown in FIG. 3G, connection members (308) may comprise sutures (312) or similar such material.

Again, it is important to note that while certain variations of attachment members have been described just above as having one or more anchoring components or one or more connection members, the attachment members described here need not have any such features. Indeed, in some variations of the devices described here, the attachment member simply comprises a strip or piece of material, as depicted in FIG. 3A, for example. Of course, it should be understood that this material may be of any length, thickness, and size, and in some instances approximates the connection members just described.

Generally, the expandable member may be any structure capable of assuming an expanded configuration and an unexpanded configuration. In some variations, the expandable member is non-inflatable and the expandable member changes between its configurations upon the application of a force to the expandable member. In some variations, however, the expandable member changes between its configurations upon the application of a stimulus to the expandable member. In some variations, the expandable member comprises hinged portions that may rotate away from a base portion when the expandable member changes to its expanded configuration. In other variations, the expandable member may comprise flexible flaps that may bend or flex away from a base portion when the expandable member changes to its expanded configuration. In still other variations, the expandable member may comprise hinged portions that rotate with respect to each other when the expandable member changes to its expanded configuration.

In some variations, one or more attachment member may apply a force to the expandable member, and this force may cause the expandable member to change between its unexpanded and expanded configurations. In some of these variations, this force may be a tensile force. In other variations, the application of a stimulus to the expandable member causes the expandable member to change between its unexpanded and expanded configurations. In some of these variations, one or more of the attachment members may provide the stimulus. In other variations, the stimulus is not provided by the attachment members. In some variations, the expandable member naturally returns to its original configuration when a force or stimulus is no longer applied to it. In other variations, a different force or stimulus may be applied to expandable member to return it to its original configuration.

Figure 4A:
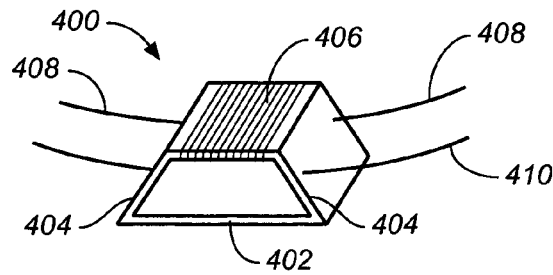
FIGS. 4A-4G are different views of a variation of an expandable member having hinged portions and a base portion.
Figure 4B:
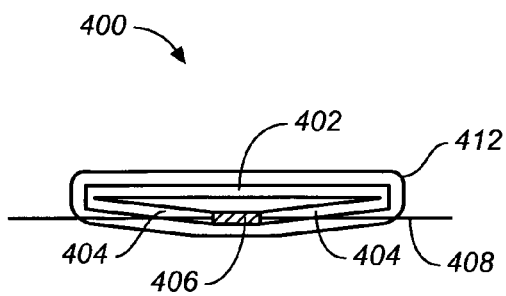

FIGS. 4A-4G show one variation of expandable member (400). Shown in FIG. 4A is a perspective view of expandable member (400), including base portion (402), two hinged portions (404), and expandable membrane (406). Also shown there are attachment members (408) connected to expandable member (400). While shown in FIGS. 4A-4C as having connection members (410), attachment members (408) may have any configuration of elements as described above. FIG. 4B shows a side view of expandable member (400) in its unexpanded configuration. Also shown there is cover (412). When expandable member (400) is in its unexpanded configuration, the hinged portions (404) lay substantially parallel to the base portion such that, in this variation, the expandable member (400) is substantially flat.

Figure 4C:
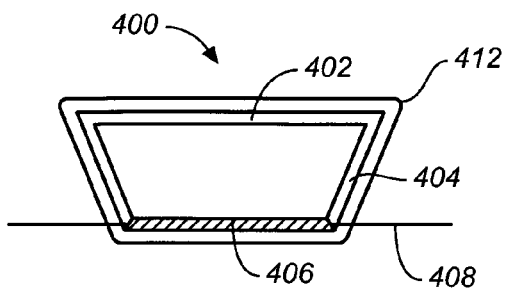

Hinged portions (404) are capable of rotating relative to the base portion (402), and may rotate away from the base portion (402) when a tensile force is applied to the hinged portions (404). Upon rotation of the hinged portions (404), as shown in FIG. 4C, the expandable member (400) changes from its unexpanded configuration to its expanded configuration, which in this variation, is substantially trapezoidal in shape. It should be appreciated however, that if enough rotation is achieved, the expandable member (400) may be rectangular in shape when in its expanded configuration. Expansion from its unexpanded configuration to its expanded configuration may allow the expandable member (400) to apply a compressive force to a target tissue (not shown). While shown in FIGS. 4B and 4C as having base portion (402) positioned above attachment members (408), the base portion (402) may be placed in any suitable configuration. Indeed, the base portion (402) may be positioned below the attachment members (408), as shown in FIG. 4A, or may be positioned in the same plane as attachment members (408).

Hinged portions (404) and base portion (402) may be made of any suitable biocompatible material. Examples of suitable materials, include, but are not limited to silicone, polypropylene, polyethylene, polyester, polycarbonate, polyetheretherketone, polyurethane, polyvinyl chloride, polyethylene terephthalate, and stainless steel. In some variations, the materials include autologous tissue, homologous tissue, cadaveric tissue, xenograft tissue, collagen matrix materials, synthetic materials, and combinations thereof. In some variations, the materials include a mesh. In some variations, the hinged portions (404) and base portion (402) include a shape-resilient material, which acts to return the expandable member (400) from its expanded configuration to its unexpanded configuration. In some variations the materials include a stimulus responsive material. The stimulus responsive material may be any material capable of changing its shape or orientation upon application of stimulus to that material. In these variations, application of at least one stimulus to the expandable member (400) may cause the expandable member (400) to change from its unexpanded configuration to its expanded configuration, or vice versa. The at least one stimulus may be one or a combination of any number of suitable stimuli, so long as they do not irreparably harm human tissue. Examples of suitable stimuli include, but are not limited to, changes in temperature, changes in pH, optical stimuli (including light), RF energy, microwave energy, electrical energy, magnetic energy, mechanical energy, and combinations thereof.

Figure 4D:
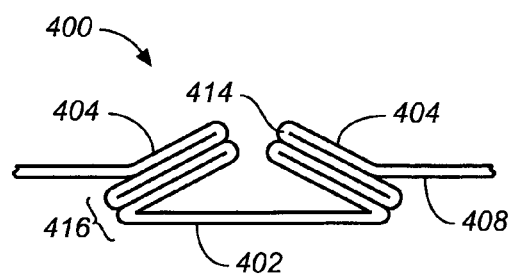

In some variations, hinged portions (404) and base portion (402) are made from different materials. In other variations, hinged portions (404) and base (402) are made from the same material. Indeed, the hinged portions (404) and base portion (402) may be formed from a single piece of material, so long as hinged portions (404) are still able to rotate with respect to base portion (402). In some of these variations, the material is thinner at the juncture between the hinged portions (404) and the base portion (402), thereby allowing rotation. In variations that include a mesh (414) or other flexible material, as shown in FIG. 4D, the mesh (414) may be folded to create the hinged portions (404). In these variations, the hinged portions (404) may be created by any number of folds (416) within the mesh (414) as may be necessary to provide a given thickness or rigidity. These folds (416) may be secured to one another by any acceptable mechanism, including but not limited to, adhesives, staples, sutures, barbs, pins, tacks, screws, rivets, VELCRO, weld joints, molded protrusions, interlocking or snap-fit features, and the like. Furthermore, additional materials (stiffener elements) may be incorporated into the mesh (414) to increase strength or rigidity.

Figure 4E:
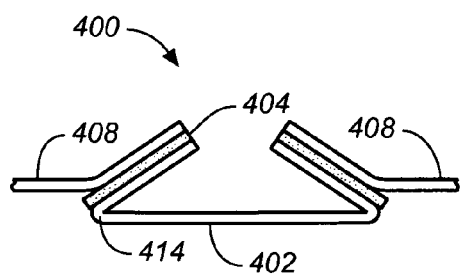

In other variations, the hinged portions (404) and base portion (402) are formed from different pieces of material and are connected in such a way that allows the hinged portions (404) to rotate with respect to the base portion (402). In some of these variations, the hinged portions (404) are connected to the base portion (402) using a mechanical hinge. In other variations, the hinged portions (404) are connected to the base portion (402) by a flexible material formed or attached between hinged portions (404) and base portion (402). This flexible material may be any suitable material, including, but not limited to a mesh or an elastomer. In still other variations, the base portion (402) itself may be made of a flexible material. In some of these variations, as shown in FIG. 4E, the base portion (402) is made of a mesh (414).

Figure 4F:
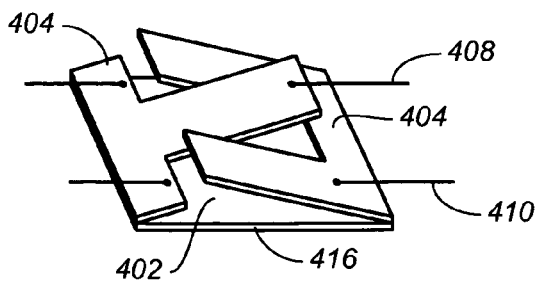
Figure 4G:
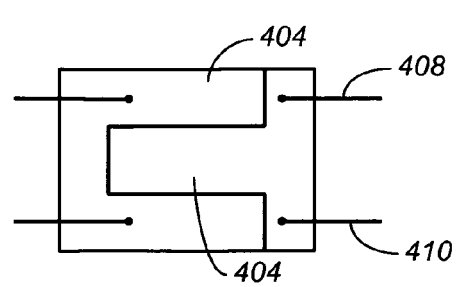

While shown in FIG. 4A as being approximately rectangular in shape, hinged portions (404) may have any suitable shape or geometry. In some variations, as shown in FIG. 4F, the hinged portions (404) may be shaped such that the ends of one or both of the hinged portions (404) extend beyond the midline of base portion (402). In some of these variations, the hinged portions (404) may also be complimentarily shaped, as shown from a top view in FIG. 4G, thereby allowing the hinged portions (404) to lay substantially flat when the expandable member (400) is in its unexpanded configuration.

While shown in FIGS. 4B and 4C as being attached to the ends of hinged portions (404), the attachment members (408) may be attached to the expandable member (404) in any suitable location. In some variations, the attachment members (408) are attached in such a way to allow for the expansion of expandable member (404) upon the application of force to the attachment members (408). Indeed, attachment members (408) may be attached anywhere along the length of hinged portions (404). In variations where the expandable member comprises a cover (412), the attachment members (408) may be attached to the hinged portions (404) through the cover (412). In other variations, attachment members (408) may be attached to the cover (412) itself, with the cover (412) in turn being attached to hinged portions (404). In variations where expandable member (404) includes an expandable membrane (406), the attachment member may (408) be attached to the expandable membrane (406).

The expandable member may include or comprise a cover, but need not. The cover may serve to protect certain components in or of the expandable member from interference from bodily fluids and tissue ingrowth, while still allowing the expandable member to expand from its unexpanded configuration to its expanded configuration. In some variations, the cover may serve to provide support to a target tissue when the expandable member is in its expanded configuration. In other variations, the cover may serve to provide a cushion between part or all of the expandable member and surrounding tissue. The cover may be made from any suitable biocompatible material. Examples of suitable materials, include, but are not limited to, silicone. In some variations, the cover loosely envelops the expandable member. In other variations, the cover may be fixed to a portion of the expandable member.

In some variations, the cover envelops the entire expandable member, but this need not be the case. Indeed, the cover may surround only a portion of the expandable member. Similarly, multiple covers may surround different portions of the expandable member. In still other variations, the cover may comprise one or more platforms. These platforms may be made from one or more flexible or rigid materials, and may provide support to a target tissue when the expandable member is in its expanded configuration.

The expandable member may also include one or more expandable membranes, but need not. The expandable membrane may help return the expandable member to its unexpanded configuration when a force is no longer being applied to the expandable member. In some variations, the expandable membrane may become stretched when the expandable member changes from its unexpanded configuration to its expanded configuration. In these variations, the expandable membrane may have a natural tendency to return to its unstretched state, and may provide a restorative force to the expandable member. This restorative force, in turn, may help to return the expandable member to its unexpanded configuration. For example, in variations where the expandable member (400) comprises hinged portions (404), as shown in FIG. 4B, an expandable membrane (406) may be attached between the hinged portions (404). When a force causes the hinged portions (404) to rotate away from the base portion (402), as shown in FIG. 4C, the expandable membrane (406) may become stretched. When a force is no longer keeping the expandable member (400) in its expanded configuration, the restorative force created by the expandable membrane (406) may cause the hinged portions (404) to rotate toward the base portion (402), thereby returning expandable member (400) to its unexpanded configuration.

In some variations, the expandable membrane may further provide direct support to a target tissue when the expandable member is in its expanded configuration. For example, in variations including hinged portions (404), as shown in FIG. 4A, the expandable membrane (406) may be positioned between the hinged portions (404) such that when the expandable member (400) is in its expanded configuration, the expandable membrane (406) creates a flat surface on which a target tissue may rest.

The expandable membrane may be made of any biocompatible material that is sufficiently elastic to allow expandable member to expand to its expanded configuration. In some variations, however, the expandable membrane may act to limit the extent to which the expandable member can expand. In some variations, the expandable membrane may be made from a material that is capable of returning to its original size and shape after it has been stretched. In some variations, the expandable membrane comprises a mesh.

Where the expandable member contains hinged portions, as described above, the expandable membrane may be attached to the device in any number of suitable configurations. In some variations, as shown in FIGS. 4A-4C, expandable membrane (406) is connected between the ends of two hinged portions (404). Alternatively, the expandable membrane (406) may still connect two hinged portions (404), but may be attached anywhere along the length of each hinged portion (404). In other variations, the expandable membrane (406) may connect a hinged portion (404) to a base portion (402). In still other variations, the expandable membrane (406) may connect two attachment members (408), or may connect an attachment member (408) to a hinged portion (404) or a base portion (402). In other variations, multiple expandable membranes (406) may be attached in any of the ways described above. In still other variations, the expandable membrane (406) may connect three or more portions of the expandable member (400). For example, the ends of the expandable membrane (406) may be attached to the hinged portions (404) while another portion of the expandable membrane (406) may be attached to the base portion (402).

In some variations, the expandable member may comprise other structures that may help to return the expandable member from its expanded configuration to its unexpanded configuration. In some variations, the expandable member may comprise one or more springs. In other variations, the expandable member may comprise strips, bands, or chords of elastic materials. These springs or materials may be attached to the expandable member in any suitable configuration as described above.

Figure 5A:
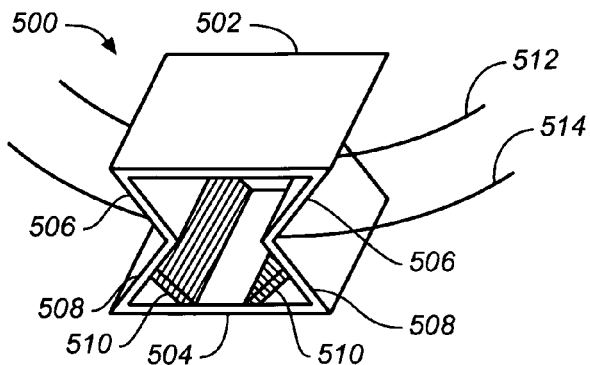
FIG. 5A is a perspective view of a variation of an expandable member having hinged portions and two base portions.
Figure 5B:
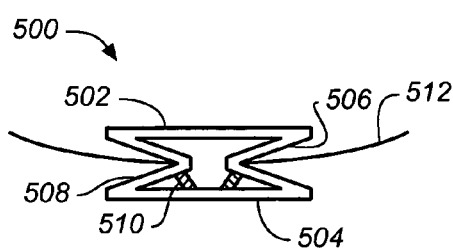
FIGS. 5B and 5C are side views of the expandable member shown in FIG. 5A.
Figure 5C:
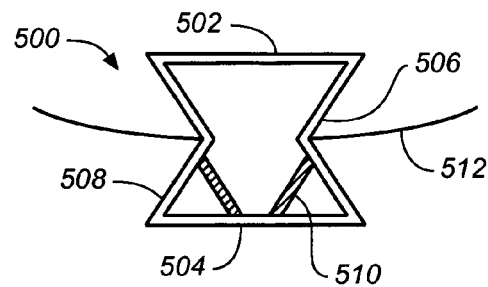

FIGS. 5A-5C illustrate another variation of expandable member (500). FIG. 5A shows a perspective view of expandable member (500) in its expanded configuration, including top (502) and bottom (504) base portions, top (506) and bottom (508) hinged portions, and expandable membranes (510). Also shown there are attachment members (512) attached to expandable member (500). Although the attachment members (512) are shown in FIG. 5A as having a thickness approximating a suture and thus approximating a connection member, the attachment member need not have a separate connection member itself. In this variation, the attachment member comprises two separate attachment members (512, 514). Of course, any of the attachment members described here may be used with any of the variations described. FIG. 5B shows a side view of expandable member (500) in its unexpanded configuration, while FIG. 5C shows a side view of expandable member (500) in its expanded configuration.

In this variation, the top hinged portions (506) are able to rotate with respect to top base portion (502), and the bottom hinged portions (508) are able to rotate with respect to the bottom base portion (504). Additionally, each top hinged portion (506) is attached to a bottom hinged portion (508), and is able to rotate with respect to that bottom hinged portion (508). The top (506) and bottom (508) hinged portions, as well as the top (502) and bottom (504) base portions may be made from any suitable materials as described above, and can be made from a single piece of material or be assembled from multiple components. Furthermore, rotation can be achieved in any way described above.

While shown in FIGS. 5A-5C as having expandable membranes (510), expandable member (500) need not have expandable membranes (510). In variations that do have one or more expandable membranes (510), they may be attached in any configuration as described above. For example, expandable membranes (510) may be used to connect the bottom hinged portions (508), connect the top hinged portions (506), connect a top hinged portion (506) to a bottom hinged portion (508), connect a top hinged portion (506) to a top (502) or bottom (504) base portion, connect a bottom hinged portion (508) to a top (502) or bottom (504) base portion, or connect an attachment member (512) to a top (506) or bottom (508) hinged portion or a top (502) or bottom (504) base portion. One or more expandable membranes (510) may also be used to connect the joint at which a top (506) and a bottom (508) hinged portion meet to another such joint or other component of the device. Additionally, one or more expandable membranes (510) may connect the top (502) and bottom (504) base portions. In some variations, one or more expandable membranes (510) may connect three or more portions of the expandable member (500). Expandable member (500) may comprise other materials that may help to return expandable member (500) to its unexpanded configuration, such as strips, bands, or chords of elastic materials, or springs. Expandable member (500) may additionally comprise a cover, as described above, but need not.

Generally, expandable member (500) expands from its unexpanded configuration to its expanded configuration upon application of a force to the expandable member (500) by one or more of the attachment members (512, 514). While in its unexpanded configuration, the top (506) and bottom hinged (508) portions may be positioned nearly parallel or parallel to the top (502) and bottom (504) base portions. When a force is applied to the expandable member, the bottom hinged portions (508) may rotate away from the bottom base portion (504) and the top hinged portions (506) may rotate away from the top base portion (502). This rotation causes the top (502) and bottom (504) base portions to move away from each other, thereby expanding expandable member (500) to its expanded configuration. In some variations, however, this expansion may result from application of one or more stimuli to the expandable member (500).

Figure 6A:
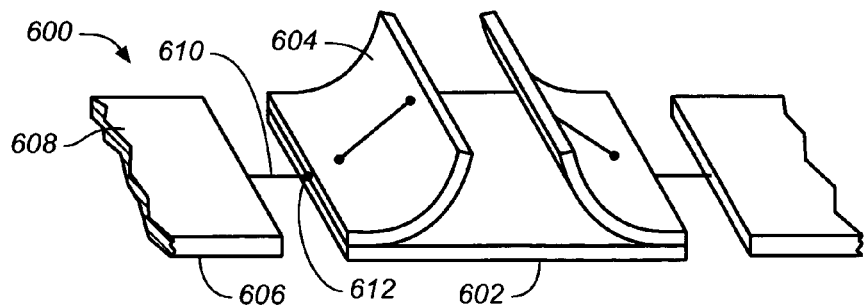
FIG. 6A is a perspective view of one variation of an expandable member with flexible flaps.
Figure 6B:
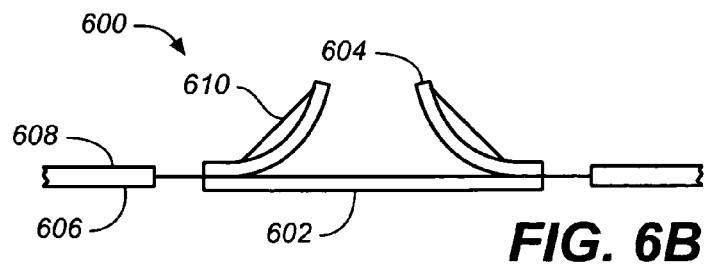
FIG. 6B is a side view of the expandable member shown in FIG. 6A.

FIGS. 6A and 6B show yet another variation of expandable member (600). FIG. 6A shows a perspective view of expandable member (600) in its expanded configuration, including base portion (602) and flexible flaps (604) and attached to attachment members (606) via connection members (610). Material (608) may be the same or different material used for connection members (610). FIG. 6B shows a side view of expandable member (600) in its expanded configuration. Again, while shown in FIGS. 6A and 6B as having connection members (610), attachment members (606) may have any configuration as described above.

When the expandable member (600) is in its unexpanded configuration (not shown), the flexible flaps (604) may lay substantially flat against the base portion (602). When one or more of the attachment members (606) applies a tensile force to the expandable member (600), the force may cause the flexible flaps (604) to flex or peel away from the base portion (602). The flexible flaps (604) may be made of any biocompatible material that is capable of bending when placed under a tensile force. Generally, the attachment members (606) are attached at or near the end of flexible flaps (604), but may be attached at any point on the flexible flaps (604) that still allows for bending of the flexible flaps (604). Additionally, the attachment member may pass through a hole or channel (612) in the expandable member (600). For example, as shown in FIG. 6A, connection members (610) are attached near the end of the flexible flaps (604) and pass through channels (612) in the expandable member (600). In some variations, the attachment members (606) may pass through an eyelet (not shown) attached to either the flexible flaps (604) or the base portion (612). In other variations, the flexible flaps (604) may bend in response to a stimulus applied to the expandable member (600). In these variations, the flexible flaps (604) may be made from a stimulus responsive material as described above.

In some variations, the flexible flaps (604) are made from a shape-resilient material that naturally acts to returns the expandable member (600) to its unexpanded configuration. Expandable member (600) may also comprise an expandable membrane or spring, as described above, to assist in returning the expandable member to its unexpanded configuration. In still other variations, expandable member (600) may comprise a material that connects the flexible flaps (604), and becomes taut when the flexible flaps (604) flex away from the base portion. This material may serve to limit the amount that the flexible flaps (604) may bend, and may also be utilized to apply a force to a target tissue. Additionally, expandable member (600) may comprise a cover, as described above, but need not.

FIGS. 7A-7E show yet another variation of expandable member (700), including first (702) and second (704) hinged portions attached at pivot point (706), and connected to first (708) and second (710) attachment members via connection members (714). Material (712) may be the same or different material used for connection members (714). Again, it should be understood that first (708) and second (710) attachment members may take on any configuration as described above.

Figure 7A:
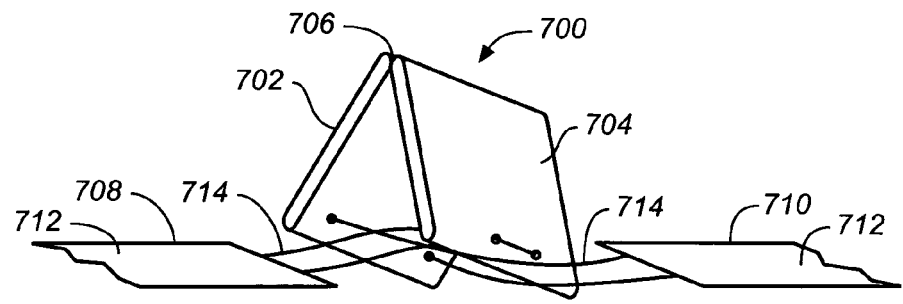
FIGS. 7A and 7B are perspective views of variations of expandable members having hinged portions.
Figure 7B:
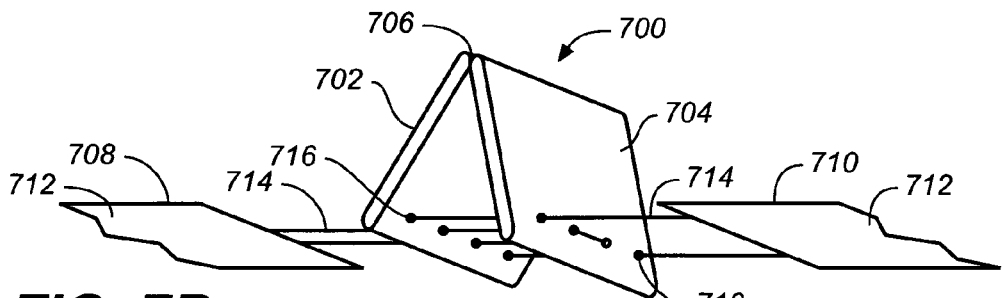

As shown in FIG. 7A, first attachment member (708) is attached to second hinged portion (704) via connection members (714) and second attachment member (710) is attached to first hinged portion (702) via connection members (714). The connection members (714) of first attachment member (708) may pass over the end of first hinged portion (702), as shown in FIG. 7A. Alternatively, the connection members (714) of the first attachment member (708) may pass through grooves (not shown) formed in the end of the first hinged portion (702). The connection members (714) of the first attachment member (702) may alternatively pass through holes (716) located within the first hinged portion (702), as illustrated in FIG. 7B. The second attachment member (710) may pass over or through the second hinged portion (704) in any of these ways. Where first (708) and second (710) attachment members both pass through and are attached through holes (716), either a separate set of holes (716) may be used for each attachment member, as shown in FIG. 7B, or the same set of holes (716) may be used for both attachment members.

Figure 7C:
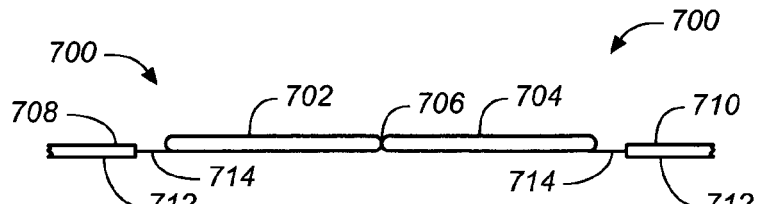
FIGS. 7C-7E are side views of variations of expandable members having hinged portions.
Figure 7D:
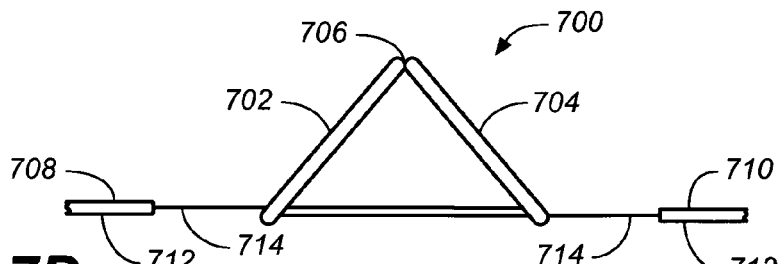
Figure 7E:
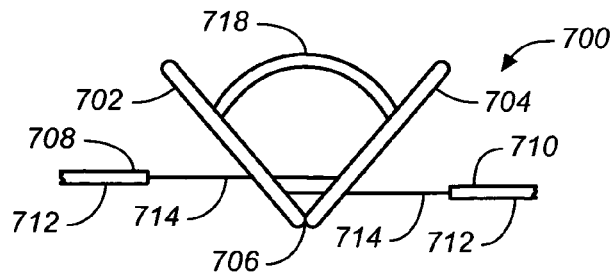

When expandable member (700) is in its unexpanded configuration, as shown in its side view in FIG. 7C, the first (702) and second (704) hinged portions may lie approximately in the same plane, and the expandable member (700) may be substantially flat. When the first (708) and second (710) attachment members apply a tensile force to the expandable member (700), the first (702) and second (704) hinged portions rotate toward each other and expand expandable member (700) to its expanded configuration. When the first (708) and second (710) attachment members are attached away from pivot point (706), as shown in FIG. 7D, this rotation may raise pivot point (706) in relation to the first (708) and second (710) attachment members. When the first (708) and second (710) attachment member are attached near pivot point (706), as shown in FIG. 7E, the rotation may raise the ends of first (702) and second (704) hinged portions in relation to the first (708) and second (710) attachment members.

The first (702) and second (704) hinged portions may be made from any suitable biocompatible material as described above, and may be capable of rotating in any way described above. The first (702) and second (704) hinged portions may be made from a single piece of material or may be assembled from different pieces. Expandable member (700) may comprise a cover, as described above, but need not. In other variations, as shown in FIG. 7E, expandable member (700) may comprise a flexible member (718) that bows upward when expandable member (700) is in its expanded configuration. Flexible member (718) may apply a force to a target tissue when it flexes outward. Additionally, the flexible member (718) may help to return expandable member (700) to its unexpanded configuration in the absence of a force applied thereto. For example, flexible member (718) may be made from a material that, while able to bend, has a tendency to return to its original shape. When a force is no longer causing first (702) and second (704) hinged portions to flex the flexible member (718), the flexible member (718) may exert a restorative force on the first (702) and second (704) hinged portions as it returns to its un-flexed shape. This restorative force may cause the hinged portions to rotate away from each other, returning the expandable member (700) to its unexpanded configuration.

Also described here are devices that provide an adjustable amount of support to a target tissue. These devices generally comprise one or more attachment members, and a non-inflatable, shape-changing portion therebetween. In some variations, the devices comprise a sling. The shape-changing portion generally has at least a first configuration and a second configuration, each having a different shape, and the shape-changing portion generally changes from the first configuration to the second configuration upon application of at least one stimulus to the shape-changing portion. In some variations, this stimulus is not applied by the attachment members. In other variations, the shape-changing portion keeps its second configuration when the at least one stimulus is removed. In some variations, the shape-changing portion is non-inflatable.

Figure 8A:
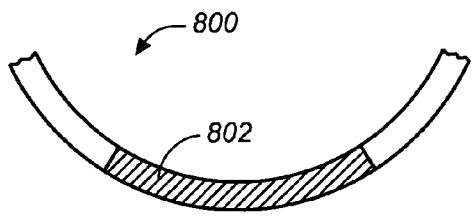
FIGS. 8A-8D are side views of variations of a shape-changing portion having length-decreasing components.
Figure 8B:
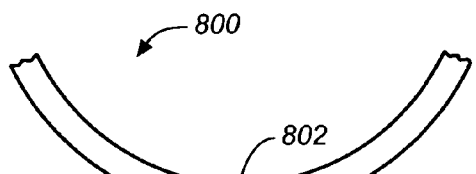

Any of the attachment members as described above may be used with these devices. Furthermore, the shape-changing portion may take on any suitable configuration. FIGS. 8A-8D show one variation of shape-changing portion (800), including length-decreasing component (802). FIG. 8A shows shape-changing portion (800) in a first configuration. Upon application of a certain stimulus to shape-changing portion (800), length-decreasing component (802) decreases in length, as shown in FIG. 8B. This decrease in length decreases the overall length of the support device, which if used as a hammock-like structure to support tissue, may increase the amount support provided by the device.

Figure 8C:
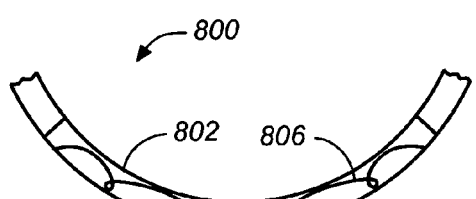
Figure 8D:
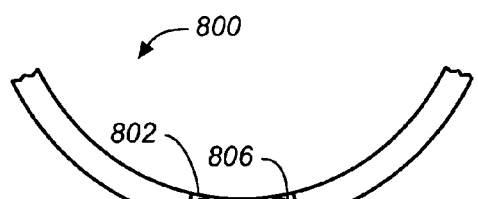

Length-decreasing component (802) may be made of any suitable biocompatible material that is capable of decreasing in length upon application of a certain stimulus. Length-decreasing component (802) may be a shape memory material that has been stretched. Examples of suitable shape memory materials include, but are not limited to, shape memory polymers and shape memory alloys such as nickel-titanium alloys, copper-aluminum-nickel alloys and copper-zinc-aluminum-nickel alloys. Alternatively, length-decreasing component may comprise a polymer gel. Examples of suitable polymer gels include, but are not limited to polyvinyl alcohol, polyacrylic acid, and polyacrylonitrile. Alternatively, length-decreasing component (802) may comprise a shape memory spring (806), as shown in FIGS. 8C and 8D. Upon application of a certain stimulus, the shape memory spring (806) changes from a first configuration, as shown in FIG. 8C, to a second configuration with a shorter overall length, as shown in FIG. 8D. Additionally, shape-changing portion (800) may contain a cover, as described above. Finally, in some variations, length-decreasing component (802) may return to its original length upon the application of a second stimulus or combination of stimuli. For example, length-decreasing component (802) may comprise a shape memory spring (806) made from a material that has a two way memory effect, and thus is capable of returning to its original shape upon application of a second stimulus.

Generally, the shape-changing portion changes from its first configuration to its second configuration upon application of at least one stimulus. The at least one stimulus may be one of or a combination of any number of suitable stimuli, so long as they do not irreparably harm human tissue. Examples of suitable stimuli include, but are not limited to, changes in temperature, changes in pH, optical stimuli (including light), RF energy, microwave energy, electrical energy, magnetic energy, mechanical energy, physical forces, and combinations thereof.

The stimulus may be applied to the shape-changing portion by any suitable device. In some variations, the stimulus is not applied to the shape-changing portion by the attachment members. In variations in which the at least one stimuli includes heat, the stimulus may be provided by electro-resistive heating. In these variations, circuits may be placed on or inside the shape-changing portion, and a current may be induced in the circuit from an outside source.

Figure 9A:
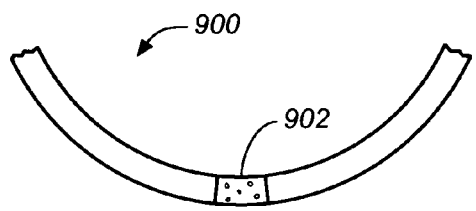
FIGS. 9A and 9B are side views of a variation of a shape-changing portion having length-increasing components.
Figure 9B:
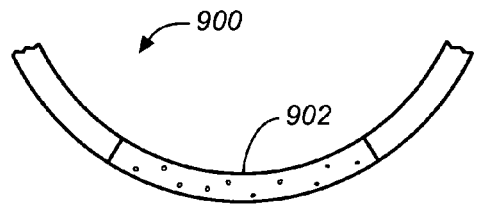

FIGS. 9A and 9B show another variation of shape-changing portion (900), with length-increasing component (902). FIG. 9A shows shape-changing portion (900) in a first configuration. Upon application of a certain stimulus, length-increasing component (902) increases in length, as shown in FIG. 9B, which increases the overall length of the device and thereby decreases the amount of support provided by the device.

Length-increasing component (902) may be made of any suitable biocompatible material that is capable of increasing in length upon application of a certain stimulus. Length-increasing component (902) may be a shape memory material that has been compressed. Examples of suitable shape memory materials include, but are not limited to shape memory polymers and shape memory alloys such as nickel-titanium alloys, copper-aluminum-nickel alloys, and copper-zinc-aluminum-nickel alloys. Alternatively, length-increasing component (902) may comprise a polymer gel. Examples of suitable polymer gels include, but are not limited to polyvinyl alcohol, polyacrylic acid, and polyacrylonitrile. Alternatively, length-increasing component (902) may comprise a shape memory spring (not shown). Upon application of a certain stimulus, the shape memory spring changes from a first configuration to a second configuration with a longer overall length. In some variations, length-increasing component (902) is capable of returning to its original length upon application of a different stimulus or combination of stimuli. For example, in variations where the length-increasing component (902) comprises a shape memory spring, the shape memory spring may be made from a shape memory material with two-way memory, as described above.

Figure 10A:
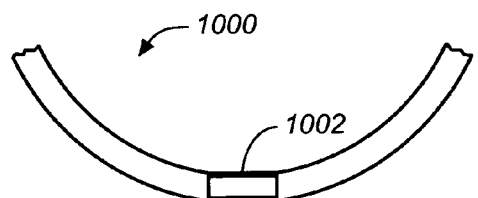
FIGS. 10A-10C are side views of one variation of a shape-changing portion having shape-changing members.
Figure 10B:
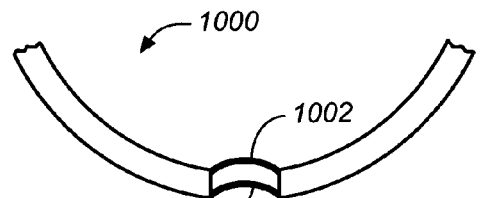
Figure 10C:
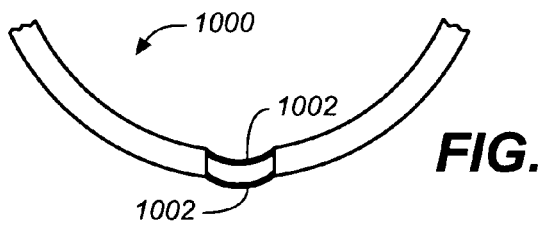

FIGS. 10A-10C show another variation of shape-changing portion (1000), including shape-changing members (1002). FIG. 10A shows shape-changing portion (1000) in a first configuration. Upon application of a stimulus, the shape-changing members (1002) take on a new shape, changing shape-changing portion (1000) into a second configuration. This second configuration may increase the amount of support provided by shape-changing portion (1000), as shown in FIG. 10B, or may decrease the amount of support provided by the shape-changing portion (1000), as shown in FIG. 10 C.

Shape-changing members (1002) may be made of any material that is capable of changing its shape upon the application of one or more stimuli. Shape-changing members (1002) may be made of a shape-memory material, as described above. Alternatively, in some variations shape-changing members (1002) comprises a length-increasing component attached to a flexible sheet. Elongation of the length-increasing component may result in bowing of the flexible sheet. In some variations, shape-changing members (1002) may return shape-changing portion (1000) to its first configuration upon application of another stimulus or combination of stimuli. For example, in variations where the shape-changing members (1002) comprise a shape-memory material, the shape-memory material may exhibit a two-way memory effect, in that a first stimulus may cause the shape-changing members (1002) to take on a second shape, but a second stimulus may cause in the shape-changing members (1002) to return to their original shape.

Figure 11A:
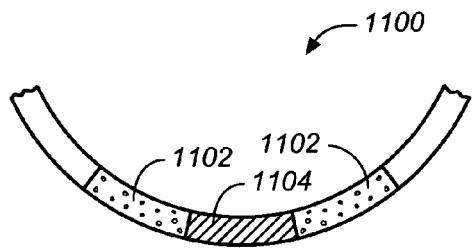
FIGS. 11A-11C are side views of one variation of a shape-changing portion having both length-increasing and length-decreasing components.
Figure 11B:
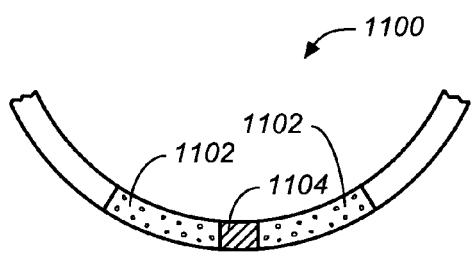
Figure 11C:
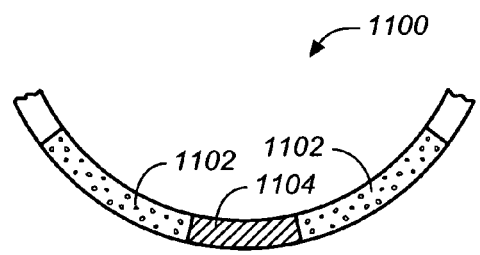

In some variations, the shape-changing portion may have a combination of length-increasing components, length-decreasing components, and shape-changing members, and may be capable of taking on multiple configurations. For example, FIGS. 11A-11C show one such variation of shape-changing portion (1100), including length-increasing components (1102) and length-decreasing component (1104). FIG. 11A shows shape-changing portion (1100) in a first configuration. Upon application of a given stimulus or combination of stimuli, the length-increasing components (1102) elongate, changing shape-changing portion (1100) into a second configuration and decreasing the amount of support provided by shape-changing portion (1100). Alternatively, application of a different stimulus or combination of stimuli may cause the length-decreasing component (1104) to contract, changing shape-changing portion (1100) into a third configuration and increasing the amount of support provided by shape-changing portion (1100).

Figure 12A:
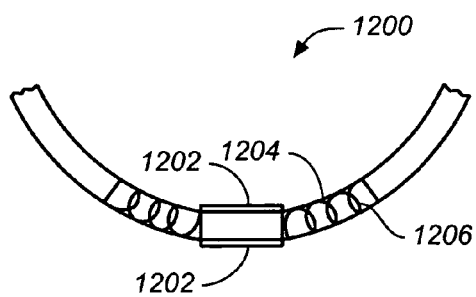
FIGS. 12A-12C are side views of one variation of a shape-changing portion having both length-increasing components and shape-changing members.
Figure 12B:
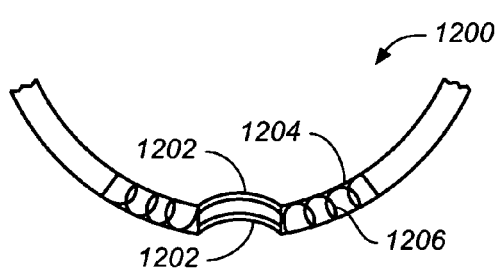
Figure 12C:
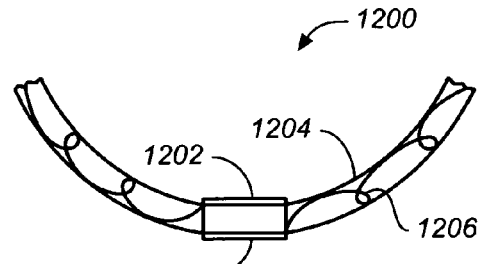

FIGS. 12A-12C show another variation of shape-changing portion (1200), including shape-changing members (1202) and length-increasing members (1204) including shape-memory springs (1206). FIG. 12A shows shape-changing portion (1200) in a first configuration. Upon application of a given stimulus, shape-changing members (1202) may change shape, as shown in FIG. 12B, thereby increasing the amount of support provided by shape-changing portion (1200). Note, however, that shape-changing members (1202) may be configured to decrease the amount of support provided by shape-changing portion (1200) when the shape-changing members change shape. Additionally, application of another stimulus may cause shape-memory springs (1206) to elongate, as shown in FIG. 12C, thereby changing shape-changing portion (1200) to a third configuration and decreasing the amount of support provided by shape-changing portion (1200).

Figure 13A:
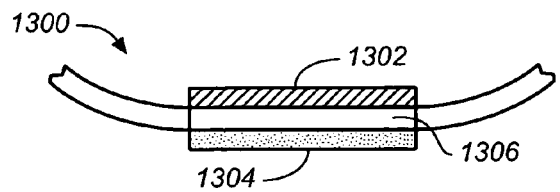
FIGS. 13A-13C are side views of one variation of a shape-changing portion having length-increasing and length-decreasing components placed in parallel.
Figure 13B:
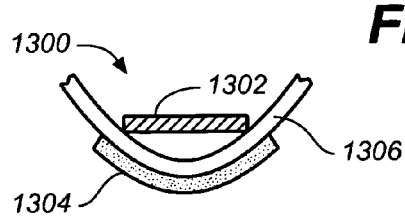
Figure 13C:
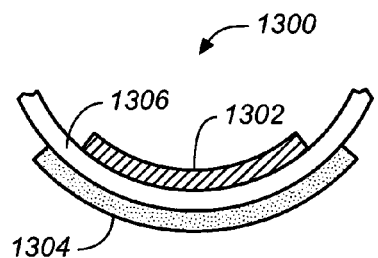

While shown in FIGS. 11A-11C and FIGS. 12A-12C as having length-increasing components, length-decreasing components, and shape-changing members placed in series, these components may be arranged in any suitable manner. Indeed, FIGS. 13A-13C show one variation of shape-changing portion (1300), including length-decreasing component (1302) and length-increasing component (1304) positioned in parallel along flexible base (1306). FIG. 13A shows shape-changing portion (1300) in a first configuration. When a certain stimulus is applied to shape-changing portion (1300), length-decreasing component (1302) decreases in length, as shown in FIG. 13B, which in turn increases the amount of support provided by shape-changing portion (1300). When a different stimulus is applied, length-increasing component (1304) may increase in length, as shown in FIG. 13C. This may in turn cause flexible base (1306) and length-decreasing component (1302) to elongate, thereby decreasing the amount of support provided by shape-changing portion (1300).

Figure 14A:
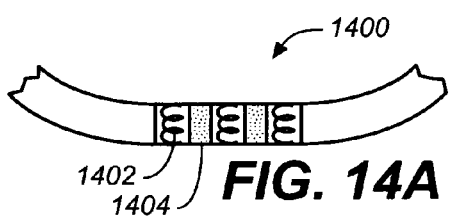
FIGS. 14A-14C are side views of another variation of a shape-changing portion having length-increasing components.
Figure 14B:
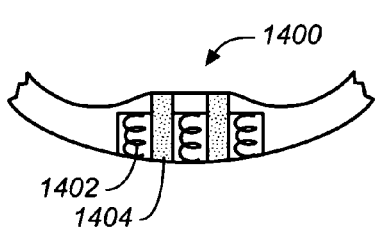
Figure 14C:
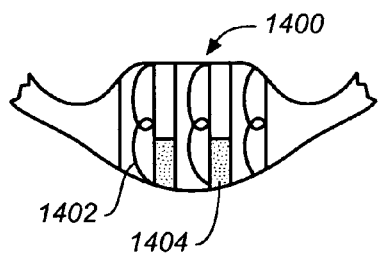

While shown in FIGS. 13A-13C to affect the length of shape-changing portion, length-increasing components and length-decreasing components may be positioned to affect the thickness of shape-changing portion. FIGS. 14A-14C show one such variation of shape-changing portion (1400), including first (1402) and second (1404) length-increasing component groups. FIG. 14A shows shape-changing portion (1400) in a first configuration. Upon application of a given stimulus, the second length-increasing component group (1404) elongates a certain amount, as shown in FIG. 14B, thereby increasing the width of shape-changing portion (1400) in a second configuration. This increase in width may provide additional support to a target tissue. Alternatively, application of a different stimulus causes the first length-increasing component group (1402) to elongate, as shown in FIG. 14C, increasing the width of shape-changing portion (1400) in a third configuration. The difference in width between the second and third configurations may depend on the length-increasing components used, and this may allow shape-changing portion (1400) to provide differing amounts of support. In some variations, shape-changing portion (1400) may contain length-decreasing components (not shown) positioned in a similar orientation. When a stimulus causes the length-decreasing component to decrease in length, this may decrease the thickness of shape-changing portion (1400).

Figure 15A:
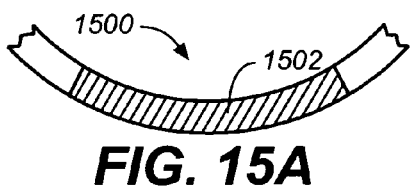
FIGS. 15A-15C are side views of one variation of a shape-changing portion having a shape-adjustable material.
Figure 15B:
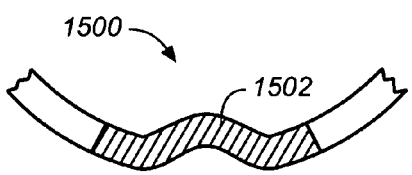
Figure 15C:
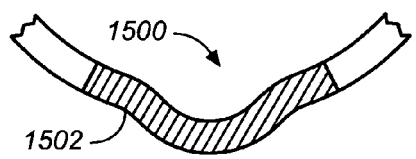

FIGS. 15A-15C illustrate yet another variation of shape-changing portion (1500), including shape-adjustable material (1502). FIG. 15A shows shape-changing portion (1500) in a second configuration. When a stimulus or combination of stimuli is applied to the shape-changing portion (1500), the shape-adjustable material (1502) may be manipulated into a second configuration. The shape-adjustable material (1502) may be adjusted to provide additional support to a target tissue, as shown in FIG. 15B, or may alternatively be adjusted to provide less support to a target tissue, as shown in FIG.

15C. When the stimulus is removed, the shape-adjustable material may retain its second configuration.

Shape-adjustable material may be any material capable of being adjusted to a second shape when a stimulus is applied to it. In some variations, this material may retain the second shape when the stimulus is removed. In some variations, the shape-adjustable material contains a thermoplastic material. Examples of suitable thermoplastic materials include, but are not limited to, polycarbonate.

Figure 16A:
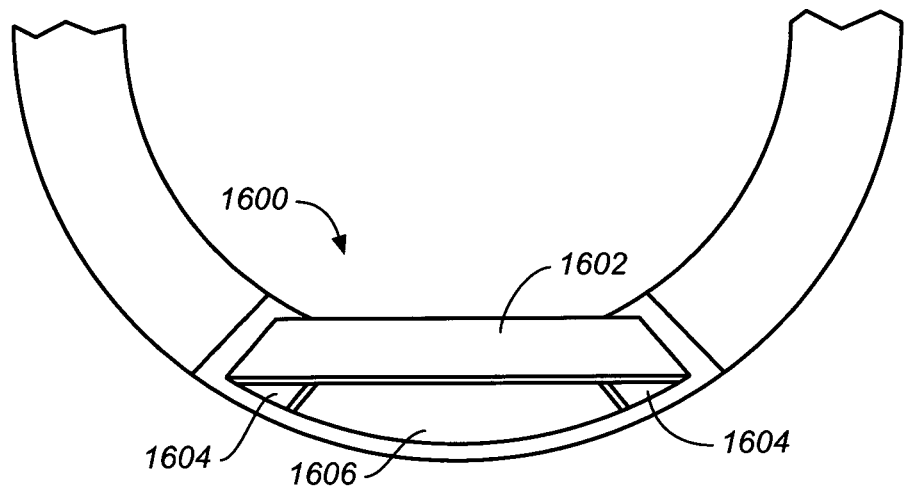
FIGS. 16A and 16B are perspective views of a variation of a shape-changing portion having a leaf spring.
Figure 16B:
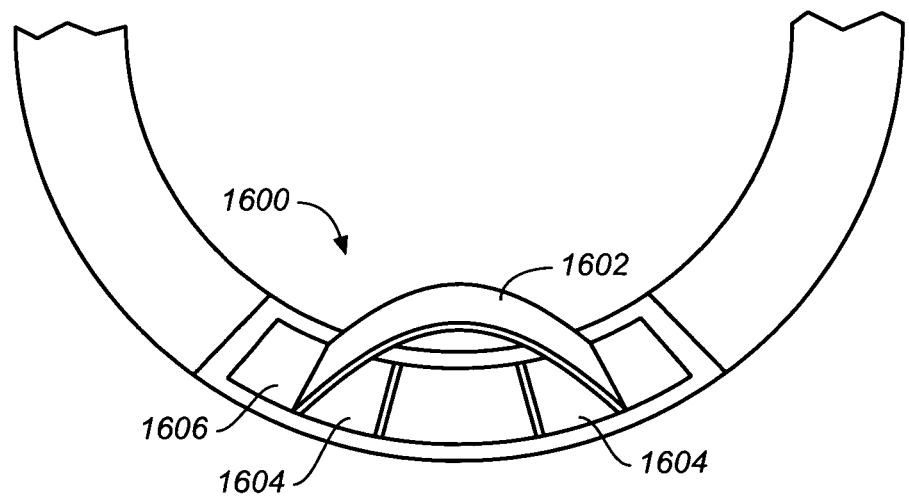

FIGS. 16A and 16B illustrate another variation of shape-changing portion (1600), including leaf spring (1602) with leaf spring anchors (1604) that are disposed within track (1606). FIG. 16A shows shape-changing portion (1600) in a first configuration. When a certain stimulus or combination of stimuli is applied to shape-changing portion (1600), the leaf spring anchors (1604) move closer together within track (1606), causing the leaf spring (1604) to bow outward. A second stimulus or combination of stimuli may then return the shape-changing portion (1600) from its second configuration to its first configuration.

Figure 17A:
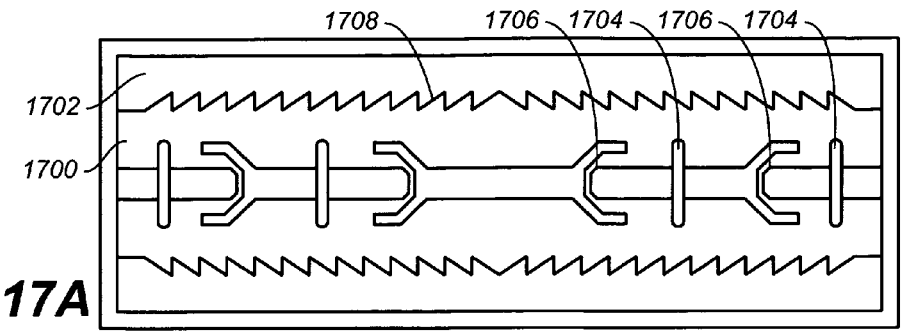
FIGS. 17A-17D are bottom views of a central locking mechanism.
Figure 17B:
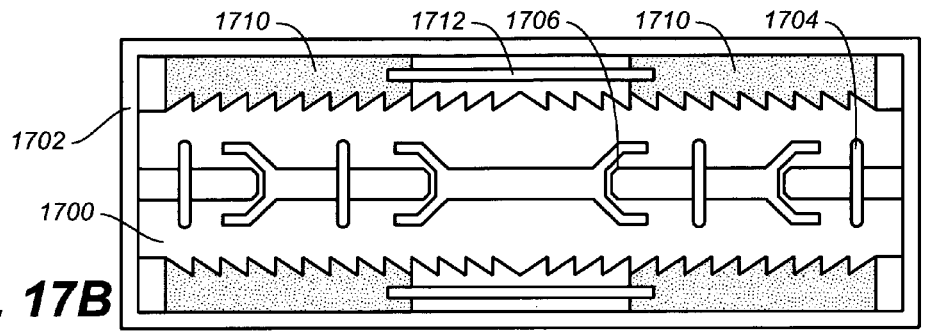
Figure 17C:
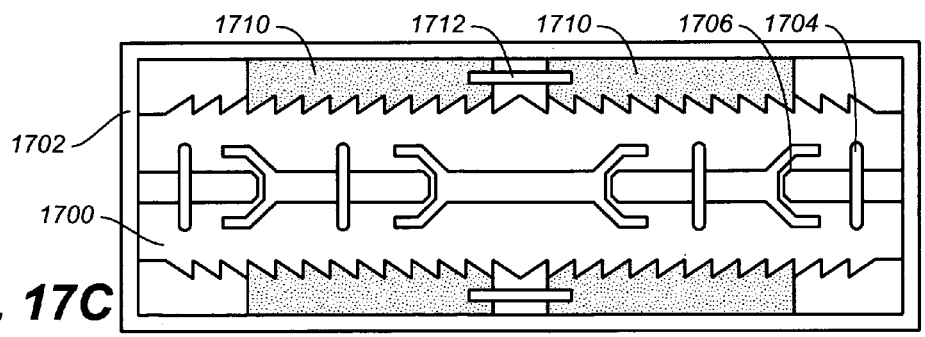

One way in which the leaf spring anchors (1604) may move within track (1606) is through the use of a central locking mechanism. FIGS. 17A-17D illustrate one variation of central locking mechanism (1700) located within track (1702). FIG. 17A shows a bottom view of track (1702) with central locking mechanism (1700), including a first shape memory material group (1704), preloaded spring elements (1706), and toothed profile (1708). FIG. 17B shows central-locking mechanism (1700) with leaf spring anchors (1710) and second shape memory material group (1712). When a certain stimulus is applied to the shape-changing portion, second shape memory material group (1712) contracts, pulling leaf spring anchors (1710) toward each other, as shown in FIG. 17C. The toothed profile (1708) allows leaf spring anchors (1710) to move incrementally toward each other, while preventing movement in the other direction caused by the leaf spring's tendency to return to the leaf spring anchors (1710) to their original configuration.

Figure 17D:
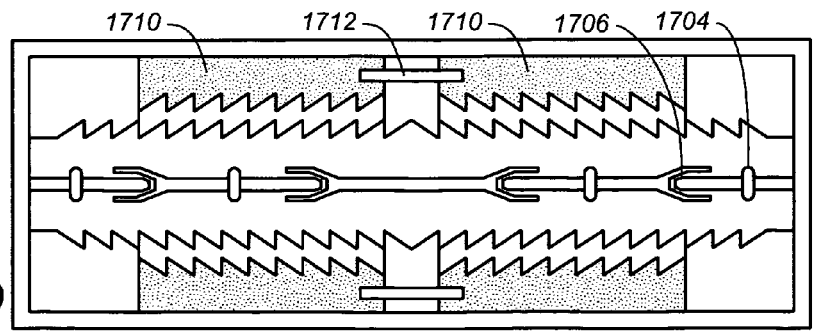

To return the leaf spring anchors (1710) to their original positions, a second stimulus may be applied to the shape-changing portion, which may cause the first shape memory material group (1704) to contract. This contraction causes the width of the central locking mechanism (1700) to decrease, as shown in FIG. 17D. With the toothed profile (1708) no longer preventing movement in the second direction, the flexed leaf spring may naturally return the leaf spring anchors (1710) to their original positions, while simultaneously elongating the second shape memory material group (1712). Once the second stimulus is removed, the preloaded spring elements (1706) may act to return the both the central locking mechanism (1700) and the first shape memory material group (1710) to their original positions.

Figure 18A:
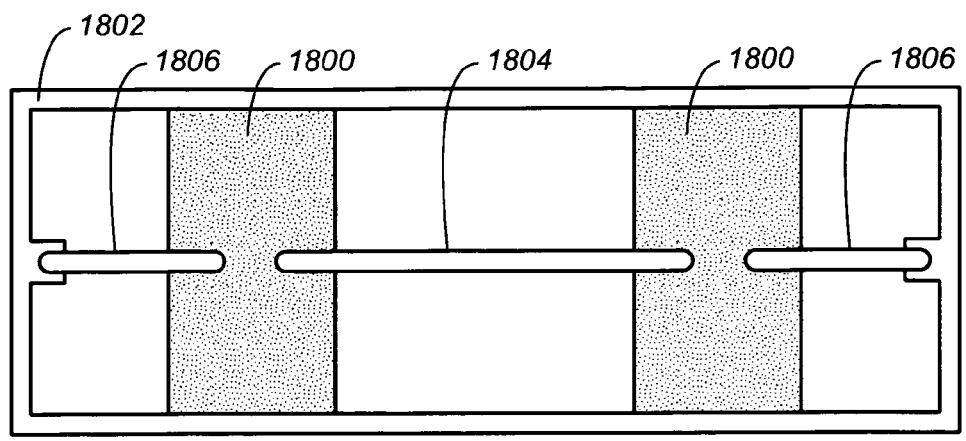
FIGS. 18A and 18B are bottom views of one variation of leaf spring anchors disposed within a track.
Figure 18B:
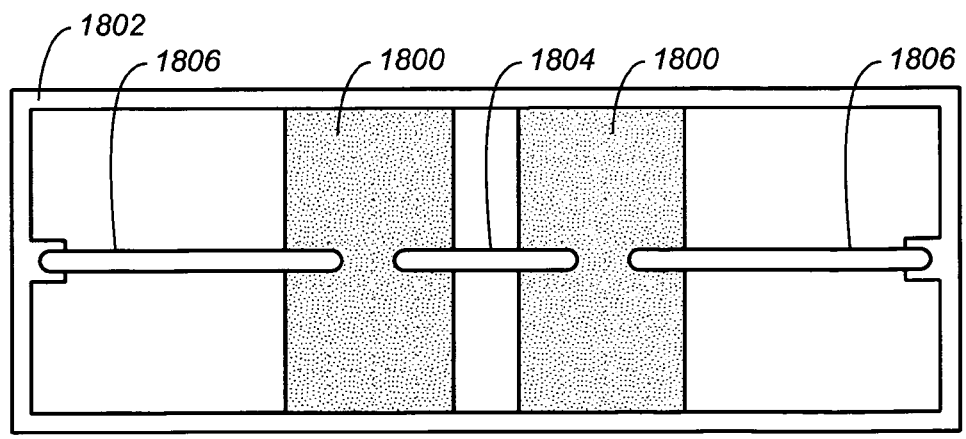

FIGS. 18A and 18B illustrate another way leaf spring anchors (1800) can be moved between their first and second configurations within track (1802). FIG. 18A shows leaf spring anchors (1800) in a first configuration. Also shown there is first shape memory material group (1804) connecting the leaf spring anchors (1800), and second shape memory material group (1806) connecting leaf spring anchors (1800) to the edges of track (1802). When a certain stimulus is applied to the shape-changing portion, the first shape memory material group (1804) contracts, bringing the leaf spring anchors (1800) closer together, as shown in FIG. 18B. This contraction may stretch the second shape memory material group (1806). A second stimulus may be applied to the shape-changing portion, which may cause the second shape memory material group (1806) to contract. This contraction may return the leaf spring anchors (1800) to return to their original positions. Furthermore, this contraction may also stretch the first shape memory material group (1804).

It should be appreciated that any of the features of the dynamic support devices described above may be incorporated into the adjustable devices described above. Alternatively, any of the features of the adjustable devices described above may be incorporated into any of the dynamic support devices described above.

Adjustable or dynamic support devices may be applied to a number of regions of the human body to provide support to a target bodily tissue. These devices may implanted in any location where providing adjustable or dynamic support is desirable, including, but not limited to, locations beneath, around, or adjacent to urethral tissue and rectal tissue. Any of the devices described above may be implanted to provide adjustable and/or dynamic support. In some methods, the devices comprise two attachment members and at least one expandable member positioned therebetween, where the expandable member has an unexpanded configuration and an expanded configuration, and where the expandable member changes from its unexpanded to its expanded configuration by application of a force to one or more of the attachment members. In these methods, the expandable member may be placed underneath the target tissue.

In other methods, the device comprises at least one attachment member for attachment to bodily tissue and at least one non-inflatable expandable member connected to the at least one attachment member, where the expandable member in its expanded configuration is configured to provide support to the target tissue. In still other methods, the device comprises at least one attachment member for attachment to bodily tissue, at least one non-inflatable expandable member, the expandable member having an unexpanded configuration and an expanded configuration, and where the at least one attachment member is configured to translate an initial force into a tensile force to expand the expandable member.

In still other methods, the device comprises one or more attachment members and a non-inflatable, shape-changing portion therebetween, where the shape-changing portion has a first configuration and a second configuration, where the shape-changing portion changes from the first configuration to the second configuration upon application of a stimulus to the shape-changing portion. In these variations, the stimulus is not provided by the one or more attachment members.

Generally, when any of the above devices are implanted, the attachment members are connected to, attached to, or integrated with bodily tissues. In some methods, one or more of the attachment members are attached to soft tissue. In other methods, one or more of the attachment members are attached to bony structures. The bony structures may be any suitable bony structure, for example, a pelvic bony structure. In still other methods, one attachment member may be attached to soft tissue while the other attachment member may be attached to one or more bony structures.

When any of the above devices are implanted to support urethral tissue, the device may be implanted by any suitable approach and in any suitable fashion. In female patients, the device may be implanted using a transvaginal approach. In male patients, the device may be implanted using a transperineal approach. FIGS. 19A-E show support device (1900) with expandable member (1902) and attachment members (1904) implanted in different fashions within a female patient having urethra (1906), vagina (1908), retropubic space (1910), pubic synthesis (1912), prepubic space (1914), and rectus fascia (1916). It is important to note that while shown in FIGS. 19A-E as a support device (1900) with expandable member (1902) and attachment members (1904), any of the devices described above may be implanted in such a fashion.

Figure 19A:
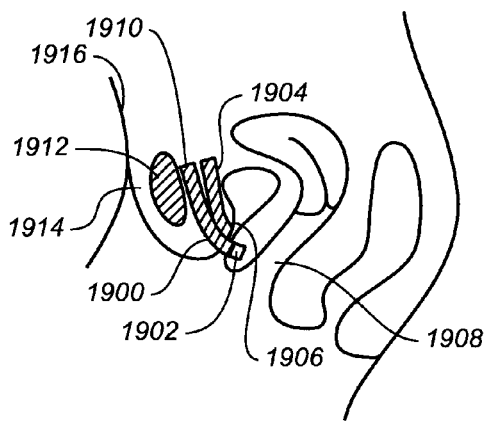
FIGS. 19A-19E are side views of variations of implantation positions for a support device.
Figure 19B:
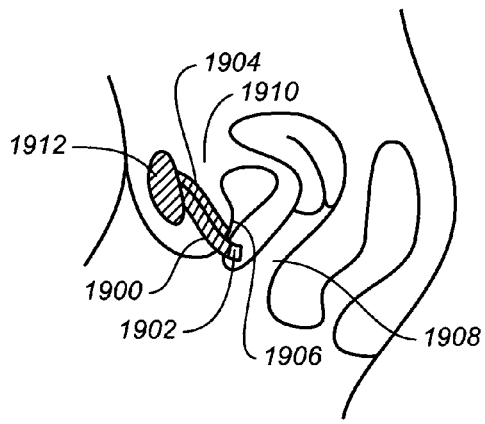

In some methods, implanting the device includes positioning the device such that the expandable member (1902) is placed beneath the urethra (1906) and above the vagina (1908) and the attachment members (1904) pass through retropubic space (1910). In some of these methods, as shown in FIG. 19A, implanting the device (1900) includes placing the ends of attachment members (1904) within soft tissues located within retropubic space (1910). In other methods, as shown in FIG. 19B, implanting the device (1900) includes attaching the ends of attachment members to pelvic bony structures, such as the pubic synthesis (1912).

To implant support device (1900) beneath the urethra (1906) in one of the above fashions, an incision is first made in the anterior vaginal wall. A surgical tool may then be used to either push or pull one attachment member (1904) into the retropubic space (1910). The attachment member (1904) may then be attached to either soft tissue or the pelvic bony tissues. Once in place, the expandable member (1902) may be positioned under the urethra (1906), and the other attachment member (1904) may be placed in a similar fashion. In some methods, the attachment members (1904) may be placed simultaneously. Additionally, the device (1900) may be adjusted once put in place. Alternatively, the device (1900) may be retrieved or repositioned if needed.

Figure 19C:
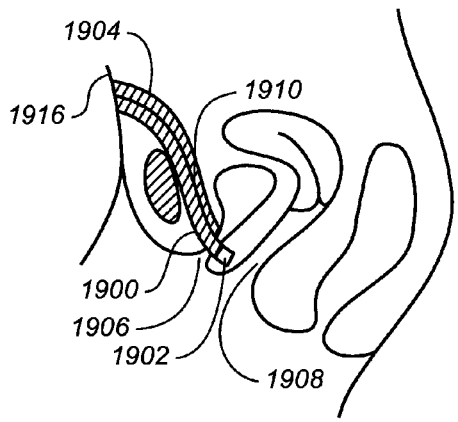

In other methods, the support device (1900) may be implanted such that the ends of attachment members (1904) pass through the retropubic space (1910) and are attached to, or pass through, a patient's rectus fascia (1916), as shown in FIG. 19C. To implant support device (1900) in this configuration, an incision may be made in the anterior vaginal wall of a female patient, and two skin incisions may be made over the rectus fascia (1916). In some methods, support device (1900) may either be pushed or pulled with a surgical device from one skin incision to the anterior vaginal incision, leaving one attachment member (1904) between the two incisions. The expandable member (1902) may then be positioned beneath the urethra (1906), and the other attachment member (1904) may be either pushed or pulled from the anterior vaginal incision to the second skin incision. Once the device (1900) is in place, it may then be adjusted, removed or repositioned.

In some methods, the device (1900) may be secured to bodily tissue. For example, sutures (not shown) may be used to attach the end of attachment members (1904) to the rectus fascia (1916) or other subdermal tissues. In other methods, sutures may be used to attach the device (1900) to the endopelvic fascia or other periurethral tissues. In methods where the ends of attachment members (1904) are passed outside of the body, these ends may be knotted outside of the body. In others of these methods, the ends of attachment members (1904) may be passed to a different location in the body. In some of these methods, the ends of the attachment members (1904) may be passed to this location through the original skin incisions, and may additionally exit the body through a second set of skin incisions. In others of these methods, the ends of attachment members may re-enter the body through a second set of skin incisions, be passed to a different location in the body, and may additionally exit the body through a third set of skin incisions.

In other methods, the expandable member (1902) may first be placed beneath the urethra (1906) through the anterior vaginal incision. One attachment member (1904) may then be pushed or pulled from the anterior vaginal incision to a first skin incision, and then the other attachment member (1904) may be pushed or pulled from the anterior vaginal incision to the second skin incision. In still other methods, the device (1900) begins disassembled, and the attachment members (1904) are passed (in either direction) between the skin incisions and the anterior vaginal incision. The expandable member (1902) may then be placed beneath the urethra, and the device (1900) assembled.

Figure 19D:
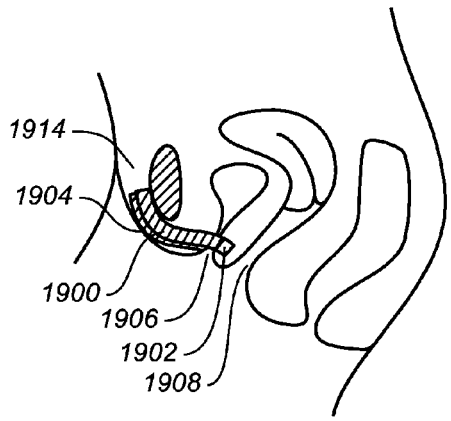
Figure 19E:
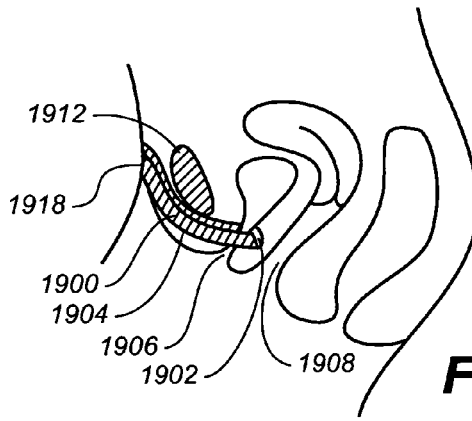

In other methods, implanting the device (1900) includes positioning the device (1900) such that at least a portion of each of the attachment members (1904) is located in the prepubic space (1914). In some of these methods, as shown in FIG. 19D, the ends of the attachment members (1904) may be placed within the prepubic space (1914). The device may be implanted by any of the methods described above, except that the attachment members (1904) will be positioned in the prepubic space (1914). In other methods, as shown in FIG. 19E, the ends of attachment members (1904) may pass through the prepubic space (1914) and may be attached to, or pass through the fascia (1918) located over the pubic synthesis (1912). The device (1900) may be implanted in this configuration by methods similar to those described above, except that the skin incisions may be made in the skin sitting over the pubic synthesis (1912).

In some methods, the device (1900) may be implanted in any of the above fashions without making skin incisions. In these methods, ends of attachment members (1904) may be tunneled to their final placement site. In these methods, attachment members comprising flaring flaps, prongs, hooks, or other anchoring components as described above, may be especially useful in maintaining positioning of the device (1900) within the body.

Figure 20A:
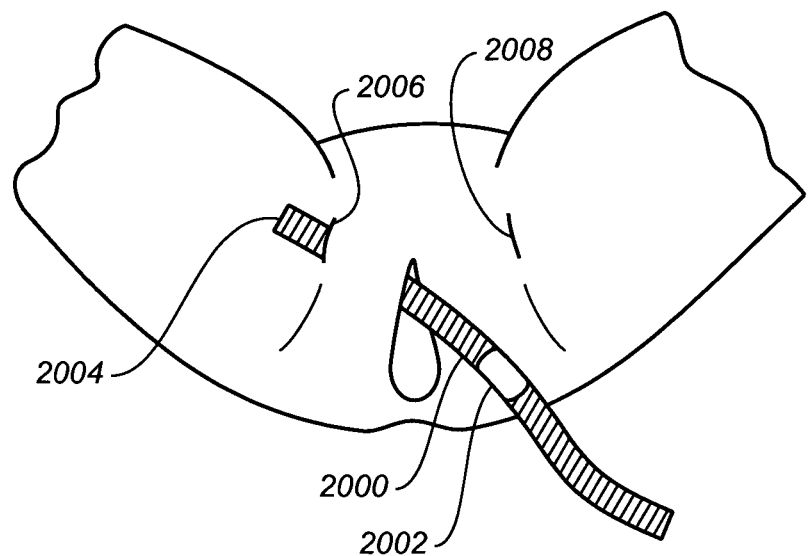
FIGS. 20A and 20B are depictions of a method by which a support device may be implanted using a transobturator approach.
Figure 20B:
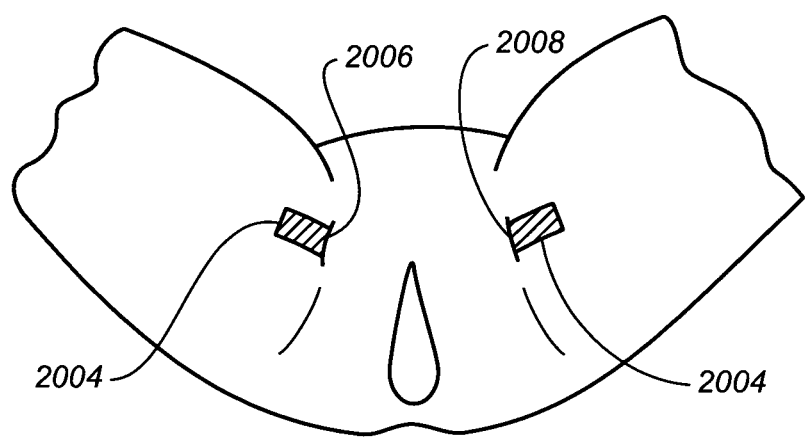

FIGS. 20A and 20B illustrate one method by which device (2000) may be implanted in a patient using a transobturator approach. While FIGS. 20A and 20B show device (2000) as having expandable member (2002) and attachment members (2004), any of the devices described above may be implanted using this method. In these methods, an incision (not shown) may be made in the anterior vaginal wall of a female patient (or the perineum of a male patient), and first (2006) and second (2008) incisions may be made in the skin over the obturator foramen. In some methods, as shown in FIG. 20A, a surgical device (not shown) may be used to either push or pull one of the attachment members (2004) from the anterior vaginal incision through a first obturator foramen (not shown) to the first skin incision (2006). The expandable member (2002) may then be placed underneath the urethra (not shown), and the other attachment member (2004) may either be pushed or pulled from the anterior vaginal incision through a second obturator foramen (not shown) to the second skin incision (2008), as shown in FIG. 20B. At this point, the device (2000) may be adjusted, removed or repositioned. In some methods, the ends of the attachment members (2004) may be cut off at the surface of the skin. In some of these methods, the attachment members (2004) are tied to the subdermal soft tissues using sutures. In other methods, the ends of attachment members (2004) may be knotted at the surface of the skin. In yet other methods, sutures may be used to attach the device to the endopelvic fascia or other periurethral, or pelvic tissues. In some methods, the central portion of the device may be anchored to the anterior vaginal wall and other periurethral tissues (in male patients, the central portion may be anchored to the bulbospongiousus muscle or other periuthethral tissues). In still other methods, the ends of attachment members (2004) may be passed to a different location in the body, as described above.

In other methods, the device (2000) may be pushed or pulled to the anterior vaginal incision through a first obturator foramen from the first skin incision (2006), leaving one attachment member (2004) between the two incisions. The expandable member (2002) may then be placed underneath the urethra (not shown), and the other attachment member (2004) may either be pushed or pulled from the anterior vaginal incision through a second obturator foramen (not shown) to the second skin incision (2008), as shown in FIG. 20B. At this point, the device (2000) may be adjusted, removed or repositioned. Alternatively, the device (2000) may begin disassembled, and the attachment members (2004) may be either pushed or pulled (in either direction) through the first and second obturator foramen between the anterior vaginal incision and the first (2006) and second (2008) skin incisions respectively. The expandable member (2002) may then be placed underneath the urethra, and the device (2000) may then be assembled and adjusted. In other methods, the device may be implanted in a similar fashion without making first (2006) and second (2008) skin incisions, and instead tunneling attachment members (2004) to their respective positions.

Figure 21A:
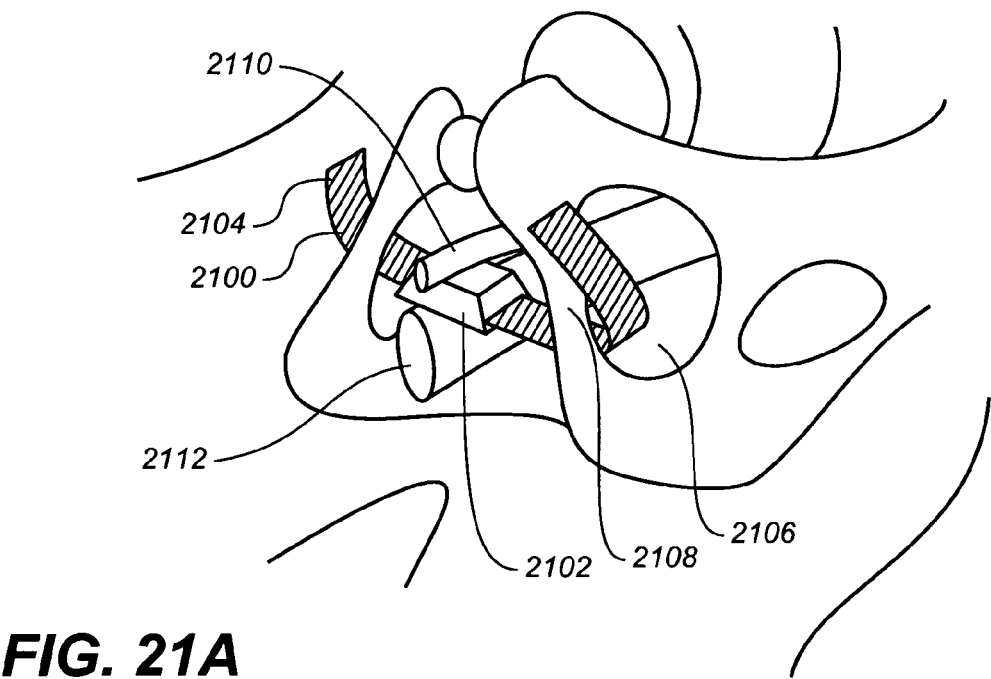
FIGS. 21A and 21B are perspective views of implantation positions for a support device.
Figure 21B:
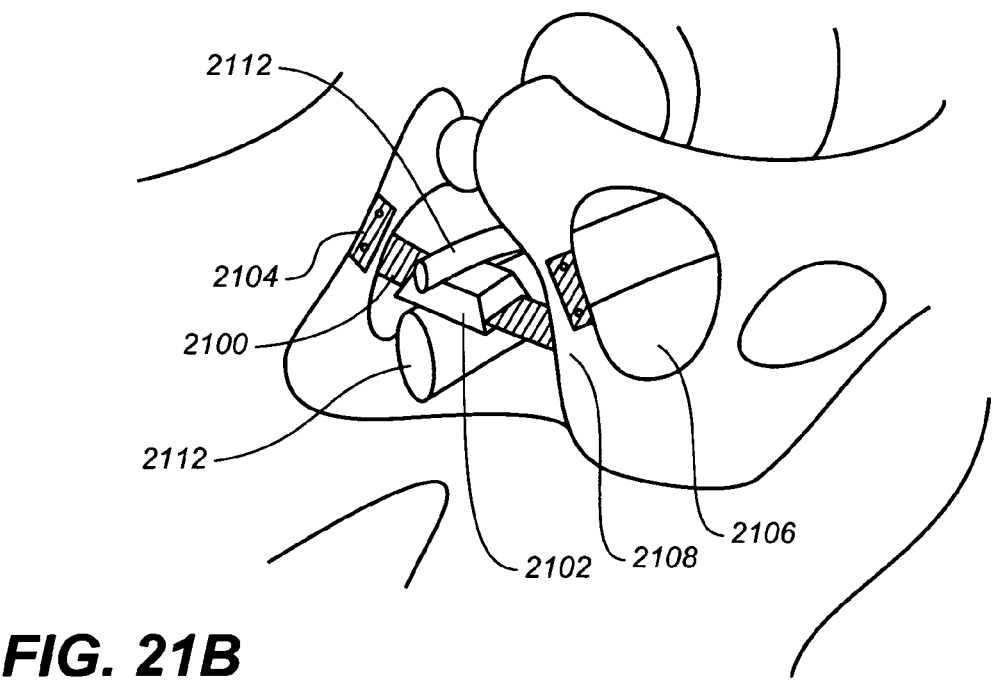

FIGS. 21A and 21B show perspective views of support device (2100) with expandable member (2102) and attachment members (2104) implanted in a female patient having obturator foramen (2106), descending pubic rami (2108), urethra (2110) and vagina (2112). Although shown in FIGS. 21A and 21B as having expandable member (2102) and attachment members (2104), the device (2100) may be any of the devices as described above. As shown in FIG. 21A, expandable member (2102) may be placed between urethra (2110) and vagina (2112), and the attachment members (2104) may pass through the obturator foramen (2106) and be attached to tissue (not shown) within or external to the obturator foramen (2106). Alternatively, as shown in FIG. 21B, the attachment members (2104) may be attached to the descending pubic rami (2108).

Any of the devices described above may also be implanted in male patients. These devices may be implanted using methods similar to those described above for female patients. Instead of the anterior vaginal wall incision made in female patients, a midline incision may be made in the perineum of male patients. This incision may be located between the scrotum and the anus, and may be between about 2 and about 5 cm in length. Dissection may then be carried down through the subcutaneous tissue to the bulbo-spongiosus muscle, which overlays the urethra. In some methods, the device may be placed external to the bulbo-spongiosus muscle. In other methods, dissection may be carried through the bulbo-spongiosus muscle, and the device may be placed internal to the bulbo-spongiosus muscle. In these methods, the device may be placed anywhere along the length of the urethra. In some methods, the device may be placed in a way to proximally relocate the urethra.

In addition, any of the devices described above may alternatively be placed above the urethra, between the urethra and the pubic symphysis. For devices placed in this manner, the attachment members may be placed in any fashion as described above.

While described above as being used to treat urinary incontinence, it should be understood that the devices described here may have broad applications in different portions of the body in order to aid in the treatment of a number of conditions. For example, the devices described here may be used to treat fecal incontinence. In treating fecal incontinence, the central portion of the device may be placed in contact with tissue at or near the anus, above and/or below the levator ani muscles. In some methods, the central portion of the device is placed between the interior and exterior sphincter muscles of the anus. In some methods, the central portion of the device may be placed externally to the exterior sphincter muscles.

The attachment members may be placed in any of the configurations as described above in relation to supporting urethral tissue. For example, the ends of the attachment members may be placed in the retropubic space, the prepubic space, may be attached to the rectus fascia, may wrap around bony structures, may be attached external to or within the obturator foramen, or may be attached to a pubic bony structure. In addition the attachment members may be wrapped around the anus and attached to themselves.

The devices described here may be implanted to support rectal tissue using any suitable method. In some methods, an initial incision may be made between the anus and the vagina (or scrotum in male patients). In other methods, an initial incision may be made between the anus and the coccyx. In other methods the device may be implanted through a lower abdominal incision. Dissection may be carried out as necessary to place the central portion of the device. In some methods, the attachment members are passed between this initial incision and skin incisions. In other methods, the attachment members are tunneled from the initial incision to a location within the body. Once placed, the device may be removed, replaced, secured or adjusted.

Also described here are kits. These kits may comprise any suitable components. For example, the kits may comprise one or more of the support devices described above, with or without additional tools (e.g., tools for implantation). The kits may also comprise instructions for using any of the kit components, or for assembling any of the kit components. In some variations, the kit includes a fully-assembled device. In other variations, the kit includes separate, unassembled components of the device. In some of these variations, the kit may also include tools to help with assembly of the device. In others of these variations, the kit may include unassembled components of different sizes or materials.

In variations where the kit comprises a device that is responsive to a stimulus, the kit may additionally include a device for providing a stimulus to the device. For example, in variations in which the device contains a circuit that provides electro-resistive heating, the kit may include a wand or other device that is capable of inducing a current into that circuit. Alternatively, if the device responds to magnetic energy, the kit may include a device that creates a magnetic field.

As noted above, the kits may also comprise tools or other materials to assist in the implantation of the device within a patient. For example, the kit may include one or more scalpels, or other cutting devices for making skin incisions. The kit may also include needles, introducers, alignment tools or guides for passing portions of the device through the body. These kits may also comprise handles, or other devices that may aid in the use and manipulation of the needles, introducers, alignment tools or guides. Furthermore, the kit may include sutures or other anchors to help affix the device within the body.

What is claimed is:

1. A device for supporting a tissue, the device comprising:
first and second flexible attachment members and at least one expandable member positioned therebetween, wherein the first and second attachment members each comprises a strip of flexible material, and wherein one or more of the attachment members comprises a mesh;
wherein the expandable member has an unexpanded configuration and an expanded configuration;
wherein the expandable member changes from its unexpanded configuration to its expanded configuration by application of a first force to one or more of the attachment members, and is configured to return to its unexpanded configuration upon removal of the first force; and wherein the device is configured to apply a supporting force to the tissue when the expandable member is in its expanded configuration, and wherein the expandable member comprises a first hinged portion attached to a second hinged portion.

2. The device of claim 1, wherein the tissue is urethral tissue.

3. The device of claim 1, wherein one or more of the attachment members is configured to translate the first force into a second force.

4. The device of claim 3, wherein the second force is substantially normal to the first force.

5. The device of claim 3, wherein the second force is a tensile force.

6. The device of claim 1, wherein the expandable member comprises a shape memory material.

7. The device of claim 1, wherein the expandable member comprises a stimulus responsive material.

8. The device of claim 1, wherein the expandable member comprises a shape-resilient material.

9. The device of claim 1, wherein the expandable member comprises one or more flexible flaps.

10. The device of claim 1, wherein the expandable member comprises a mesh.

11. The device of claim 1, wherein the expandable member is substantially flat when in its unexpanded configuration.

12. The device of claim 1, wherein the expandable member is approximately trapezoidal in shape when in its expanded configuration.

13. The device of claim 1, wherein the expandable member comprises a cover.

14. The device of claim 13, wherein the cover comprises silicone.

15. The device of claim 1, wherein one or more of the attachment members comprises polypropylene.

16. The device of claim 1, wherein one or more of the attachment members comprises an anchoring component.

17. The device of claim 16, wherein one or more of the attachment members comprises at least one connection member for connecting the anchoring component to the expandable member.

18. The device of claim 1, wherein the first and second attachment members are approximately rectangular.

19. The device of claim 18, wherein the first and second attachment members are each between about 1 and about 4 cm in width and between about 5 and about 20 cm in length.

20. The device of claim 1, wherein one or more of the attachment members promotes tissue ingrowth.

21. A device for supporting a tissue, the device comprising:
first and second flexible attachment members and at least one expandable member positioned therebetween, wherein the first and second attachment members each comprises a strip of flexible material;
wherein the expandable member has an unexpanded configuration and an expanded configuration;
wherein the expandable member changes from its unexpanded configuration to its expanded configuration by application of a first force to one or more of the attachment members; and
wherein the device is configured to apply a supporting force to the tissue when the expandable member is in its expanded configuration, and wherein the expandable member comprises first and second hinged portions attached to a base portion, wherein the first and second hinged portions are each configured to rotate away from the base portion when the expandable member changes from its unexpanded configuration to its expanded configuration.

22. The device of claim 21, wherein the expandable member further comprises an expandable membrane attached to the first and second hinged portions.

23. The device of claim 21, wherein the expandable member further comprises a third hinged portion attached to the first hinged portion and a fourth hinged portion attached to the second hinged portion.

24. A device for supporting a tissue, the device comprising:
first and second flexible attachment members and at least one expandable member positioned therebetween, wherein the first and second attachment members each comprises a strip of flexible material;
wherein the expandable member has an unexpanded configuration and an expanded configuration;
wherein the expandable member changes from its unexpanded configuration to its expanded configuration by application of a first force to one or more of the attachment members; and
wherein the device is configured to apply a supporting force to the tissue when the expandable member is in its expanded configuration, and wherein the expandable member comprises an expandable membrane, wherein the expandable membrane is stretched when the expandable member changes from its unexpanded configuration to its expanded configuration, and is configured to return the expandable member to its unexpanded configuration when the first force is removed.

* * * * *